US012661205B2

(12) United States Patent
Chi Sing et al.

(10) Patent No.: US 12,661,205 B2
(45) Date of Patent: Jun. 23, 2026

(54) NEEDLE LOCALIZATION REFLECTORS, SYSTEMS, AND METHODS

(71) Applicant: Cianna Medical, Inc., Aliso Viejo, CA (US)

(72) Inventors: Eduardo Chi Sing, Dana Point, CA (US); John E. Greene, Valley Center, CA (US); Nikolai Rulkov, San Diego, CA (US)

(73) Assignee: Cianna Medical, Inc., Aliso Viejo, CA (US)

( * ) Notice: Subject to any disclaimer, the term of this patent is extended or adjusted under 35 U.S.C. 154(b) by 107 days.

(21) Appl. No.: 17/811,744

(22) Filed: Jul. 11, 2022

(65) Prior Publication Data

US 2023/0028061 A1 Jan. 26, 2023

Related U.S. Application Data

(60) Provisional application No. 63/224,732, filed on Jul. 22, 2021.

(51) Int. Cl.
*A61B 90/00* (2016.01)
*A61B 5/06* (2006.01)

(52) U.S. Cl.
CPC .............. *A61B 90/39* (2016.02); *A61B 5/064* (2013.01); *A61B 2090/3908* (2016.02); *A61B 2090/397* (2016.02); *A61B 2090/3987* (2016.02)

(58) Field of Classification Search
None
See application file for complete search history.

(56) References Cited

U.S. PATENT DOCUMENTS

| | | | |
|---|---|---|---|
| 5,161,536 A | 11/1992 | Vilkomerson et al. | |
| 6,569,160 B1 * | 5/2003 | Goldin | A61B 18/1492 606/49 |
| 2009/0281419 A1 | 11/2009 | Troesken et al. | |
| 2010/0210939 A1 | 8/2010 | Hartmann et al. | |
| 2010/0298858 A1 * | 11/2010 | Dimmer | A61N 5/1015 606/192 |
| 2010/0312094 A1 * | 12/2010 | Guttman | A61B 34/20 600/411 |

(Continued)

FOREIGN PATENT DOCUMENTS

| | | |
|---|---|---|
| WO | 2017167594 A1 | 10/2017 |
| WO | 2020139649 A1 | 7/2020 |

OTHER PUBLICATIONS

International Search Report and Written Opinion dated Nov. 11, 2022 for PCT/US2022/073610.

(Continued)

*Primary Examiner* — Christopher Koharski
*Assistant Examiner* — Farouk A Bruce
(74) *Attorney, Agent, or Firm* — Dorsey & Whitney LLP

(57) ABSTRACT

Apparatus, systems, and methods are provided for localization of a needle within a patient's body using markers. In an exemplary embodiment, a probe includes a distal end for placement against a surface of the region and one or more antennas for transmitting electromagnetic signals into and receiving reflected signals from the region. A processor processes the modulated reflected signals at one or more of the surface locations to determine marker locations along the needle and generate a three-dimensional model of the body region and needle.

8 Claims, 18 Drawing Sheets

(56) References Cited

U.S. PATENT DOCUMENTS

| | | | |
|---|---|---|---|
| 2011/0313288 A1 | 12/2011 | Chi Sing et al. | |
| 2012/0010490 A1 | 1/2012 | Kauphusman et al. | |
| 2014/0309522 A1* | 10/2014 | Fullerton | A61B 90/39 |
| | | | 600/424 |
| 2016/0128765 A1* | 5/2016 | Schultz | A61B 18/1492 |
| | | | 606/41 |
| 2017/0020562 A1* | 1/2017 | Erkamp | A61B 34/20 |
| 2017/0172618 A1* | 6/2017 | Erkamp | A61B 90/39 |
| 2017/0319102 A1 | 11/2017 | Greene et al. | |
| 2020/0077922 A1* | 3/2020 | Greene | A61B 90/98 |
| 2021/0068705 A1 | 3/2021 | Greene et al. | |

OTHER PUBLICATIONS

European Search Report dated May 2, 2025 for EP22846747.8.
European Search Report dated Sep. 15, 2025 for EP22846747.8.

* cited by examiner

3Rx 1Tx

4Rx 1Tx

4Rx 1Tx

NEEDLE LOCALIZATION REFLECTORS, SYSTEMS, AND METHODS

RELATED APPLICATIONS

This application claims priority to U.S. Provisional Application No. 63/224,732, filed on Jul. 22, 2021 and titled, "Needle Localization Reflectors, Systems, and Methods," which is hereby incorporated by reference in its entirety.

TECHNICAL FIELD

The present disclosure relates to systems and methods for determining a location of a needle. More particularly, the present disclosure relates to identifying and/or locating markers or reflectors along a needle positioned within a patient's body to generate a model of the needle within the region for needle localization.

BRIEF DESCRIPTION OF THE DRAWINGS

These and other features, aspects, and advantages of the present disclosure will become better understood with regard to the following description, appended claims, and accompanying drawings where:

9A-9C are perspective, side, and end views, respectively, of an exemplary probe that may be included in a system.

Figures 9A, 9B:
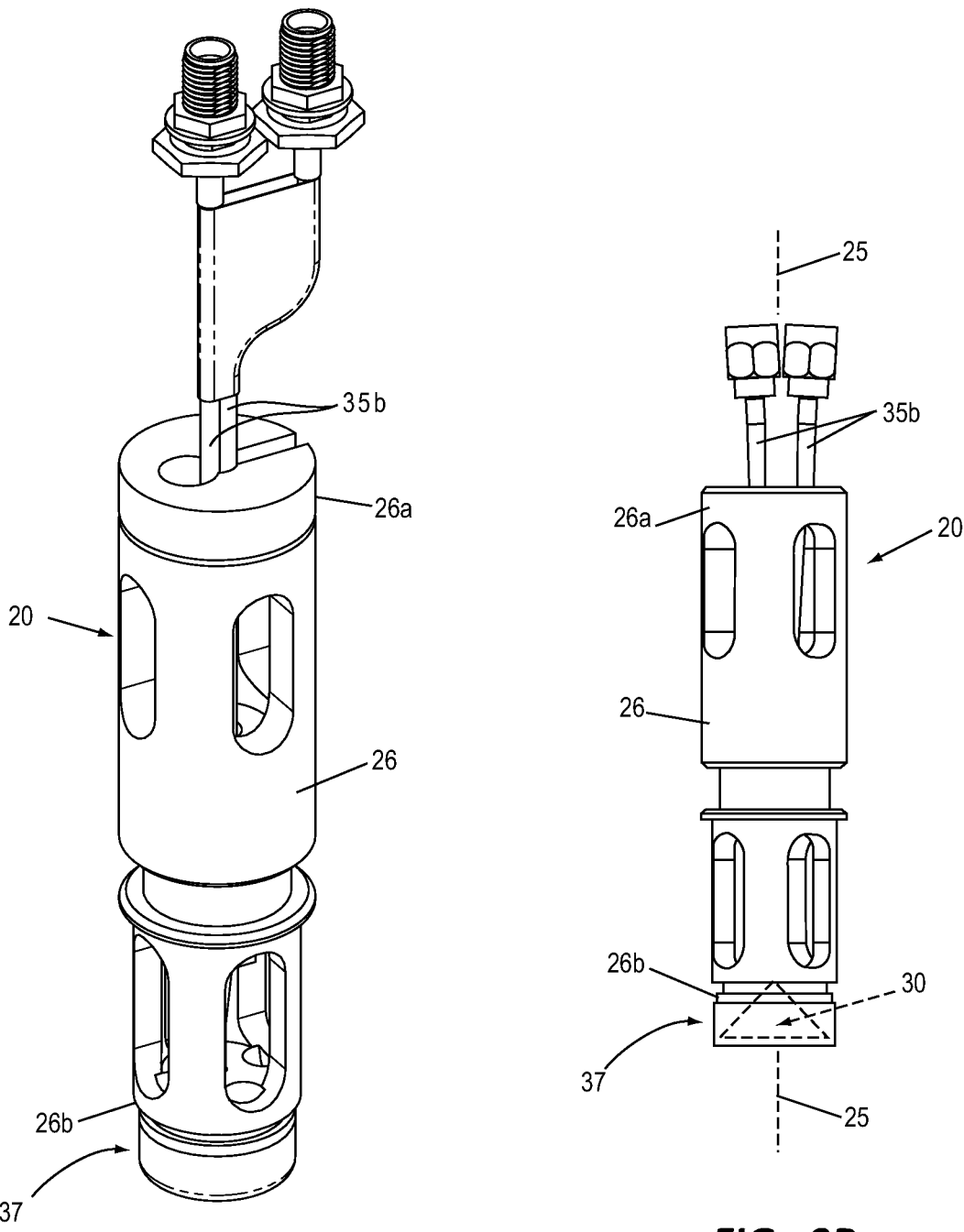
Figure 9D:
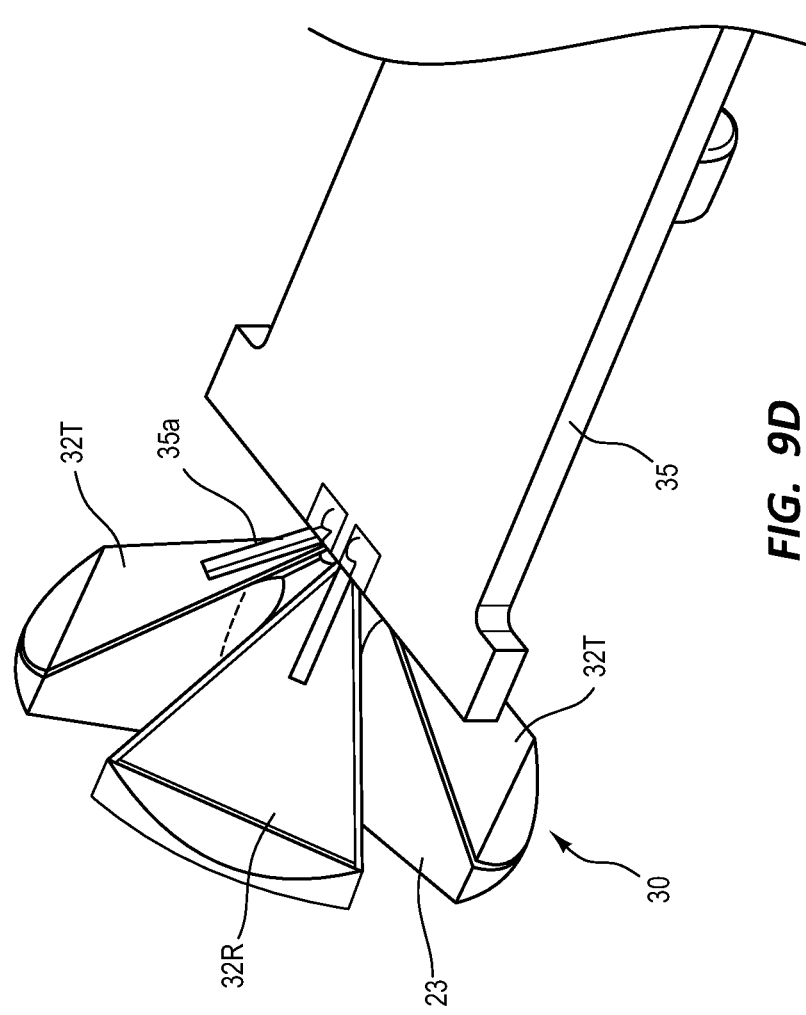
Figure 9C:
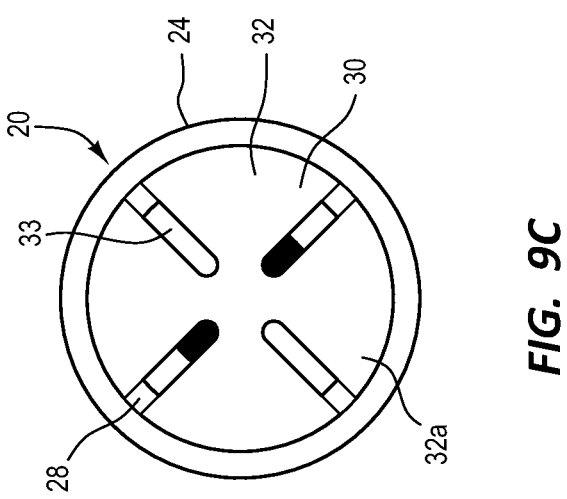

FIG. 9D is a detail of an antenna assembly that may be included in the probe shown in FIGS. 9A-9C.

Figures 10A, 10B, 10C:
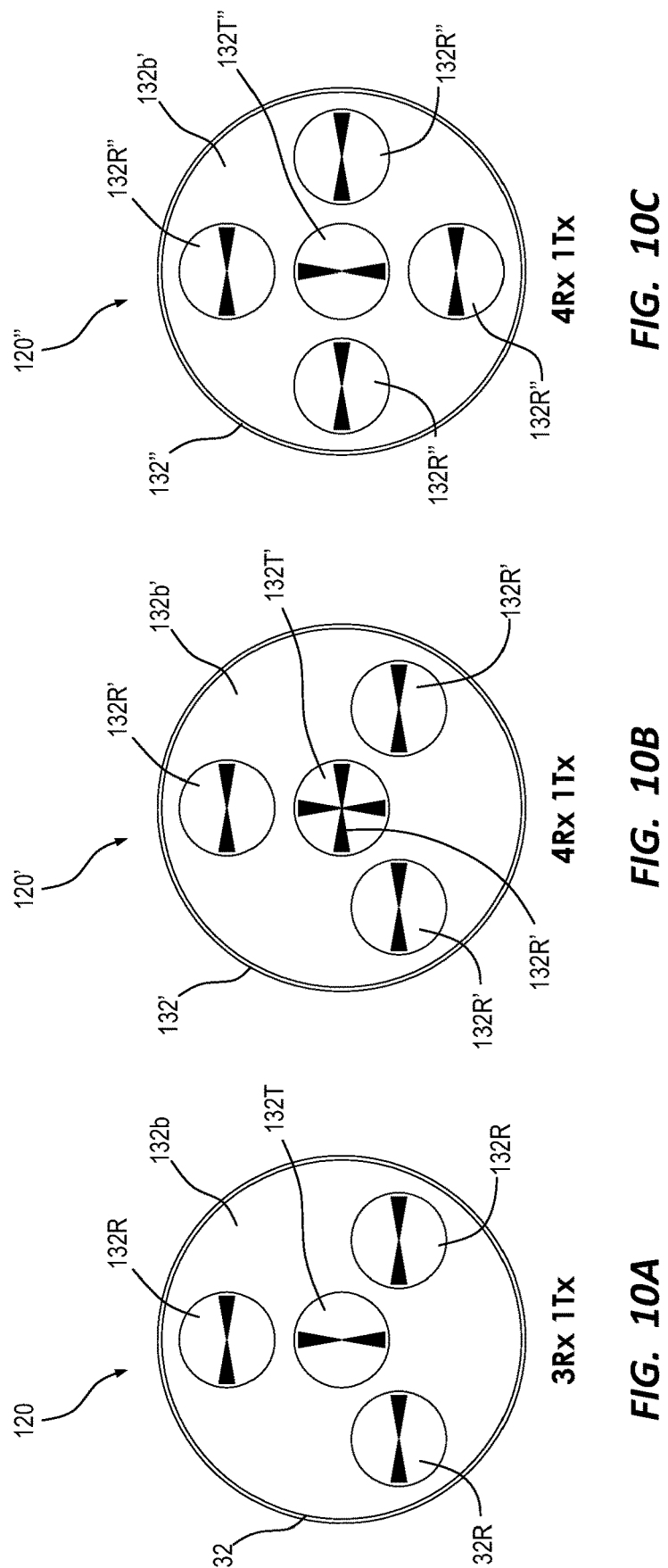

FIGS. 10A-10C illustrate different potential arrangements of the antennas on a probe.

Figure 11:
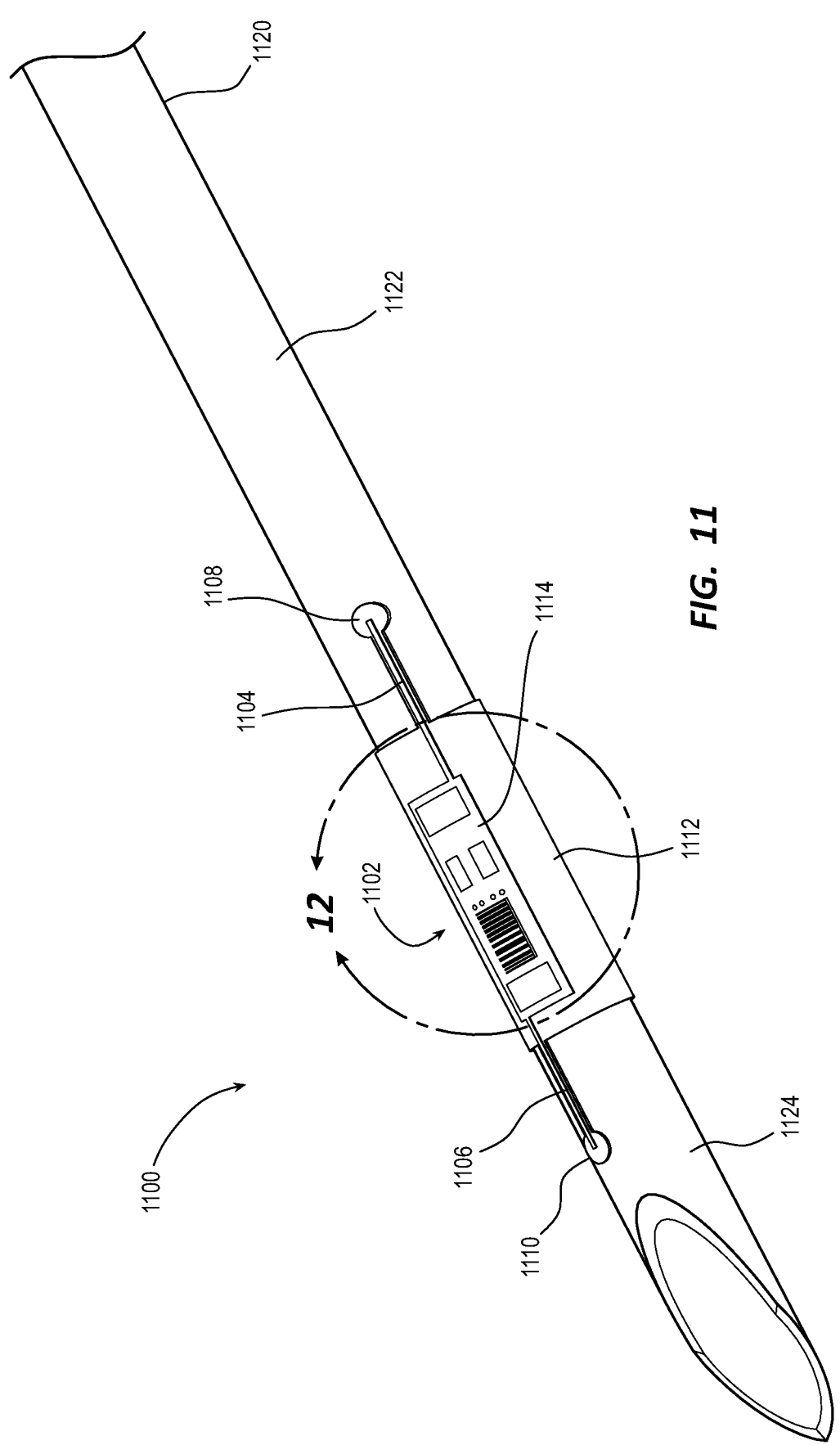

FIG. 11 illustrates an assembled needle shaft according to some embodiments.

Figure 12:
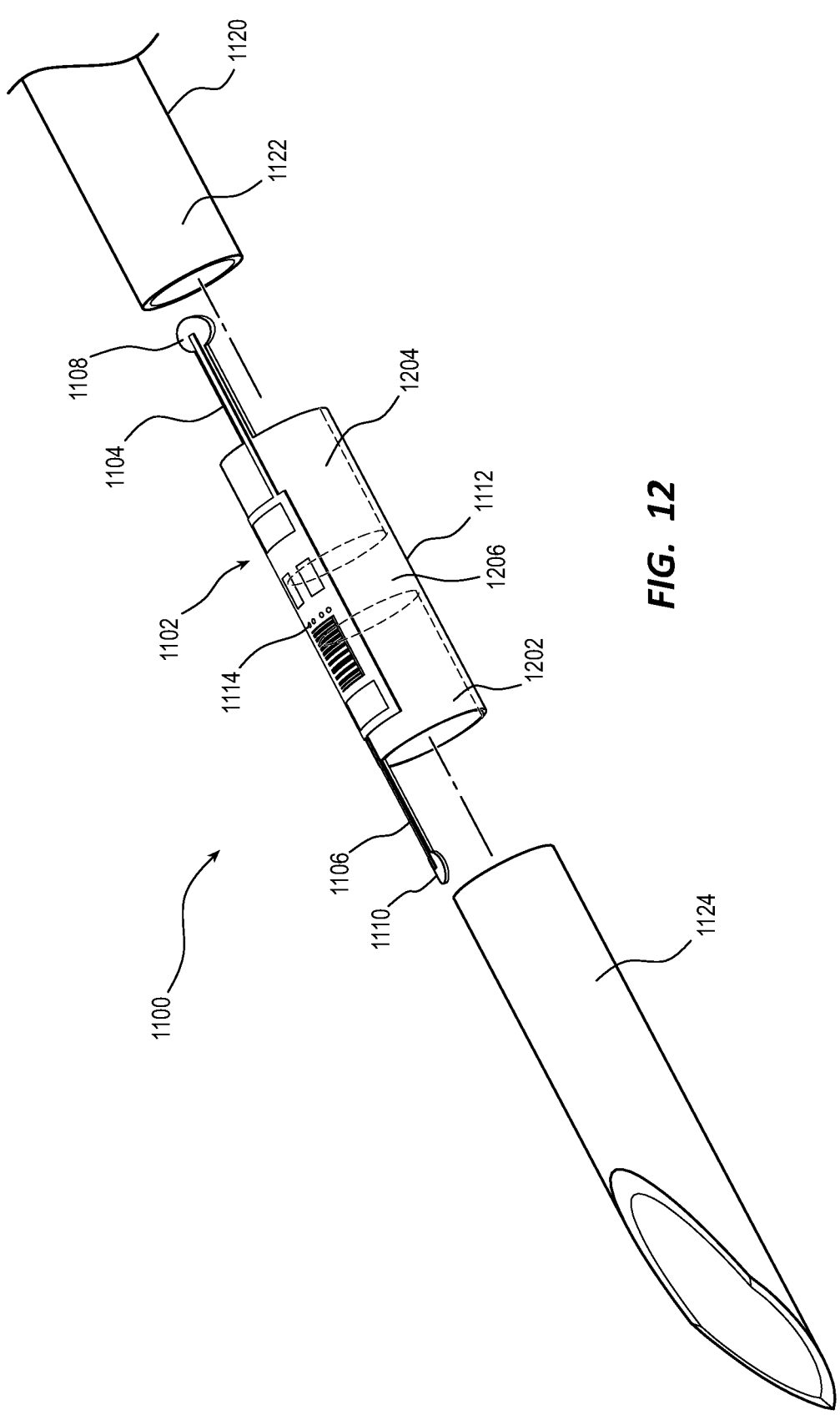

FIG. 12 is an exploded view of the needle shaft of FIG. 11.

Figure 13:
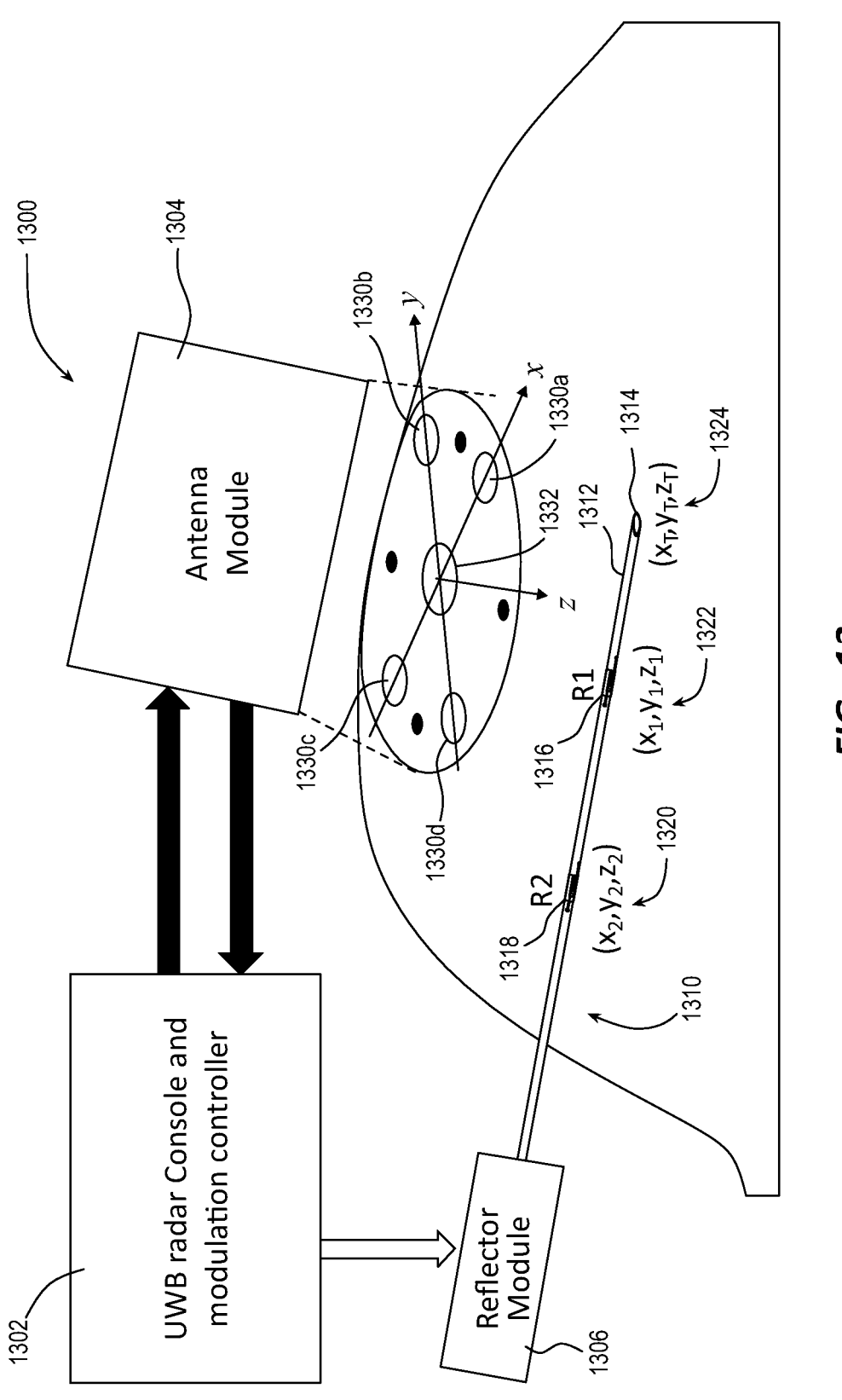

FIG. 13 illustrates a simplified block diagram of a system for localization of a needle tip using two markers.

Figures 14, 15:
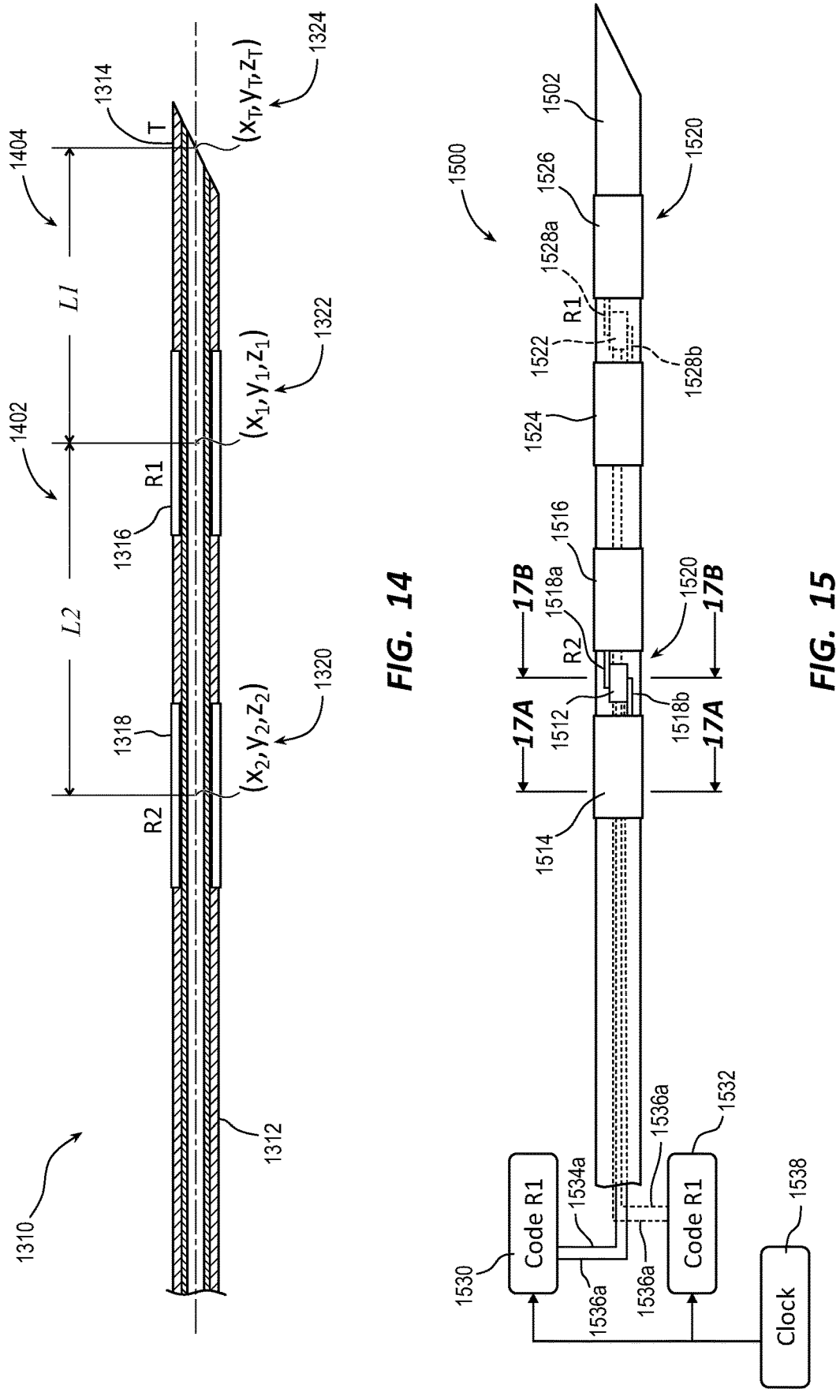

FIG. 14 is a cross-sectional view of the needle of FIG. 13.

FIG. 15 illustrates a needle comprising markers with cylindrical electrodes integrated exterior of an insulation layer surrounding a needle shaft.

Figures 16A, 16B, 16C:
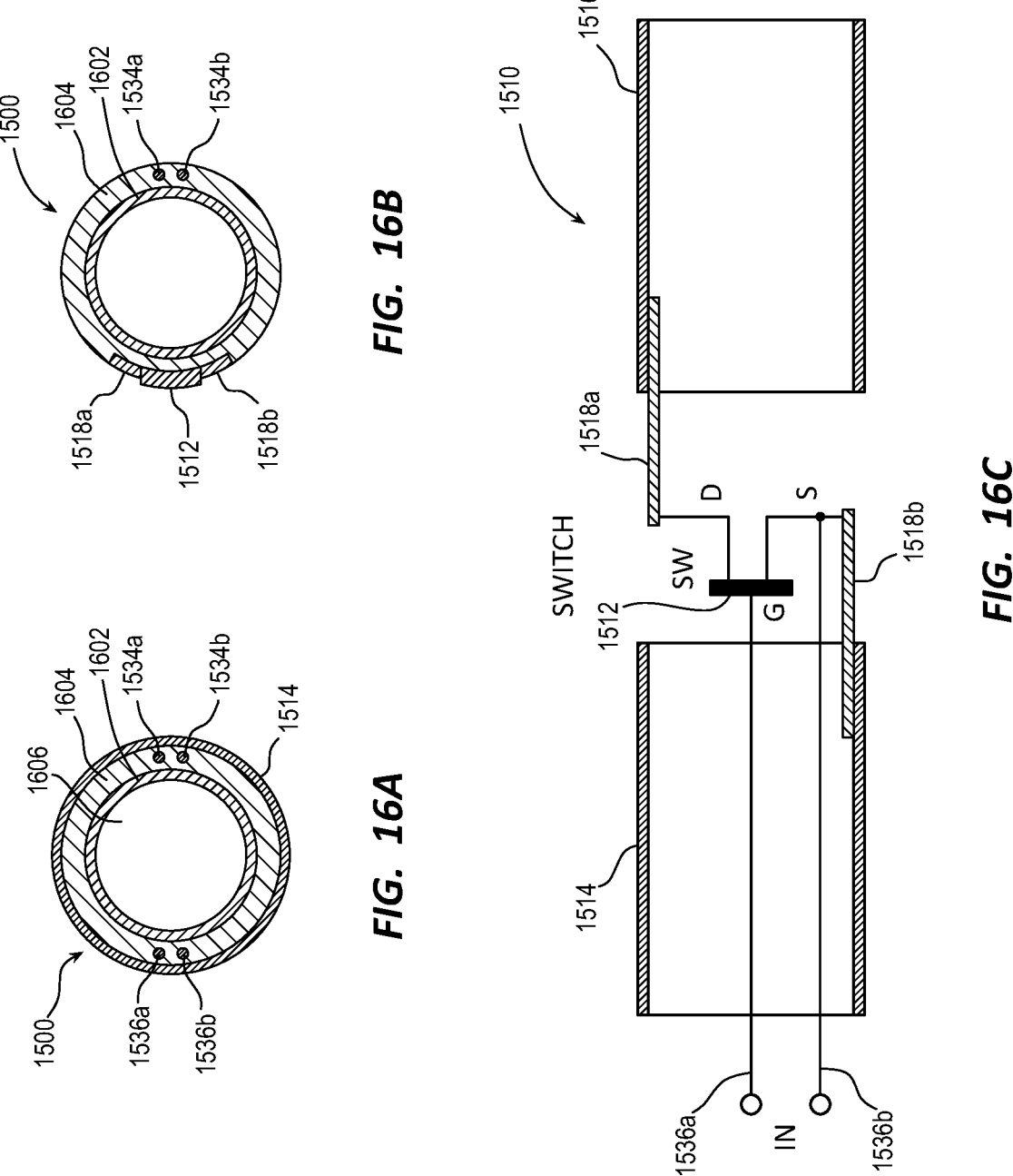

FIG. 16A illustrates a first cross-sectional view of the of the needle of FIG. 15.

FIG. 16B illustrates a second cross-sectional view of the of the needle of FIG. 15.

FIG. 16C illustrates a block diagram of a marker with cylindrical electrodes.

Figures 17, 18A, 18B, 18C:
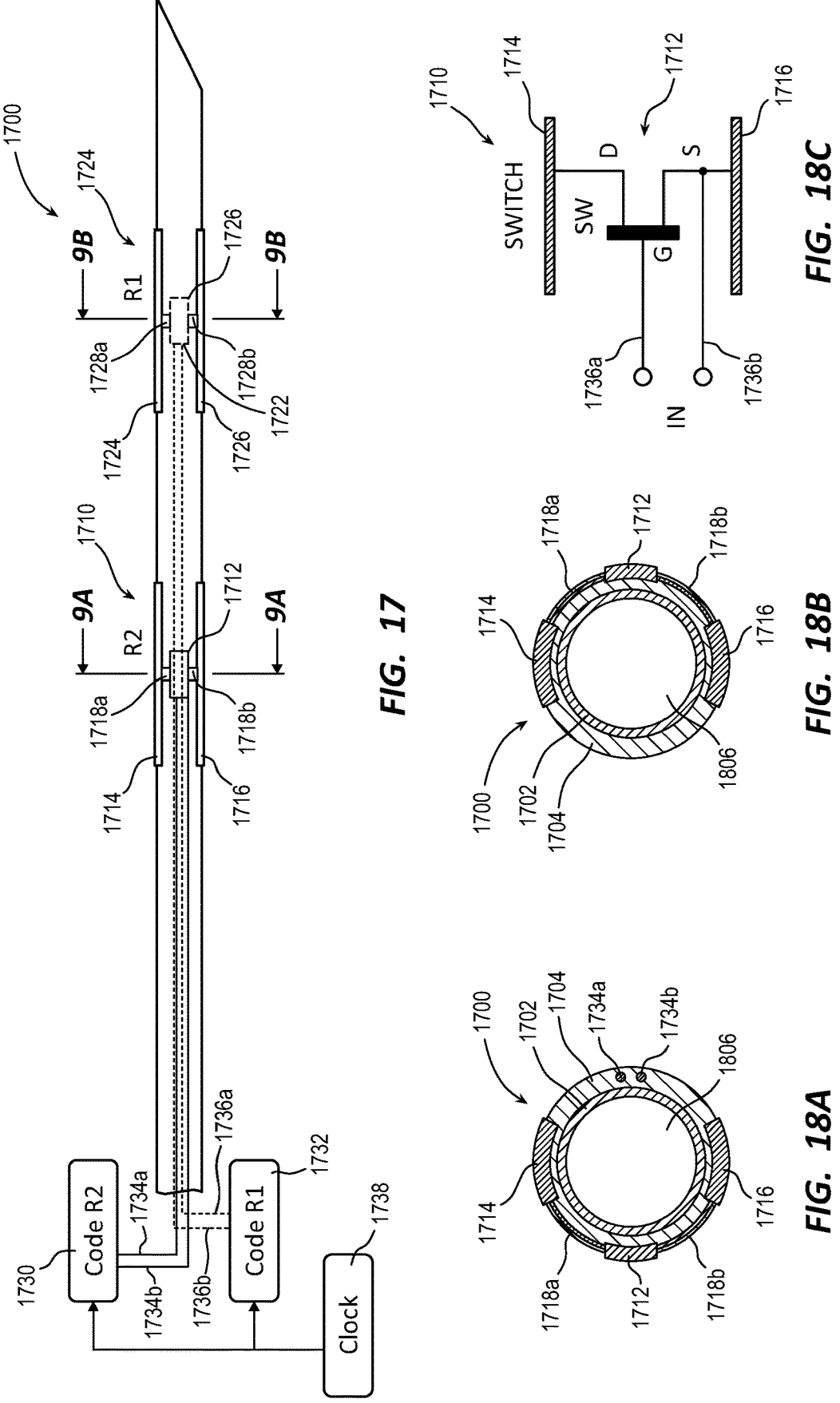

FIG. 17 illustrates a needle comprising markers with plate electrodes integrated exterior of an insulation layer surrounding a needle shaft.

FIG. 18A illustrates a first cross-sectional view of the of the needle of FIG. 17.

FIG. 18B illustrates a second cross-sectional view of the of the needle of FIG. 17.

FIG. 18C illustrates a block diagram of a marker with plate electrodes.

Figure 19:
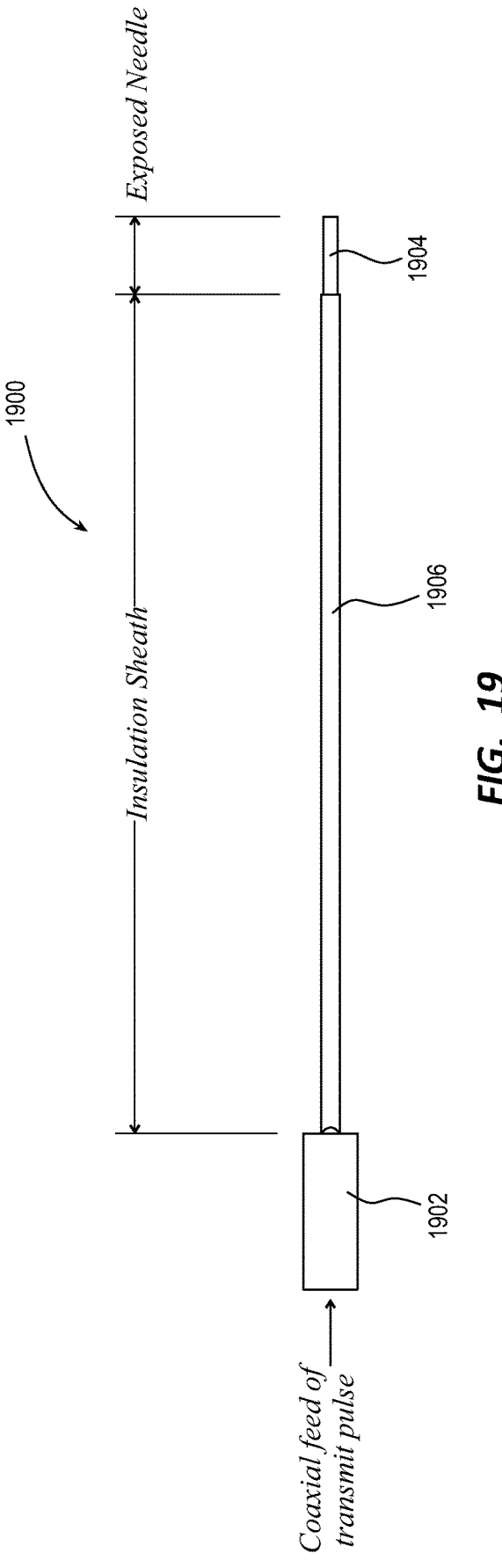

FIG. 19 illustrates an embodiment in which the needle is used to transmit a signal.

DETAILED DESCRIPTION

Described herein are embodiments for tracking the location of a needle within a patient. Some embodiments use electromagnetic signals reflected or transmitted by the needle to track the location and orientation of the needle. Needle localization may be used to assist in a variety of different procedures. For example, knowing the location of a needle may be beneficial in defining a volume of a target tissue, tracking the placement of markers implanted within the region, recording a location of a biopsy, and placing surgical devices.

Before a biopsy or surgical procedure, including procedures to remove a lesion within a breast, e.g., during a lumpectomy procedure, the location of the lesion must be identified. For example, mammography or ultrasound imaging may be used to identify and/or confirm the location of the lesion before the procedure. The resulting images may be used by a surgeon during the procedure to identify the location of the lesion and guide the surgeon, e.g., during dissection to access and/or remove the lesion. However, such images are generally two dimensional and therefore provide only limited guidance for localization of the lesion since the breast and any lesion to be removed are three-dimensional structures. Further, such images may provide only limited guidance in determining a proper margin around the lesion, i.e., defining a desired specimen volume to be removed.

To facilitate localization of the lesion, before a surgical procedure, markers may be inserted into the breast, e.g., via a needle, such that the markers are positioned at the location of the lesion and around the lesion to define the volume and the margin. With the markers placed, the patient may proceed to surgery, e.g., to have a biopsy or lumpectomy performed.

To correctly position these markers, a system may track the location of a tip of the needle. This needle location data may be used to correctly place the markers to define the volume as well as record the actual location of the placement. Further, the needle location may be used to determine the placement of a biopsy or placement of a catheter.

Accordingly, systems, apparatuses, and methods for localization of a needle in advance of and/or during surgical, diagnostic, or other medical procedures would be useful. Embodiments herein are directed to systems, apparatuses, and methods for tracking a location of a needle using electromagnetic signals. In some embodiments, markers along the needle may be used to reflect or transmit electromagnetic signals. In some embodiments, a shaft of the needle may be used for reflecting or transmitting the electromagnetic signals.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from a practitioner during use. The proximal end refers to the opposite end or the end nearest the practitioner during use.

FIGS. 1-4 show exemplary embodiments of a system 100 for identifying a location of needle 102 using actively modulated markers within a patient's body (e.g., locating the position of the needle tip 104). In these embodiments, the actively modulated markers are directly controlled by a controller 110. For example, a signal reflected by or transmitted by the needle markers is modulated by the controller 110 altering the antenna properties of the marker by sending a control signal over a cable. Thus, an actively modulated marker has a switch that is controlled via an input signal sent over a wire. In some embodiments, the actively modulated marker may be a passive reflector meaning the marker may not produce its own signal but may reflect a signal transmitted by a probe. In an exemplary embodiment, the system 100 may be used to generate a three-dimensional model of a body region of a patient including a current position of the needle.

Figure 1:
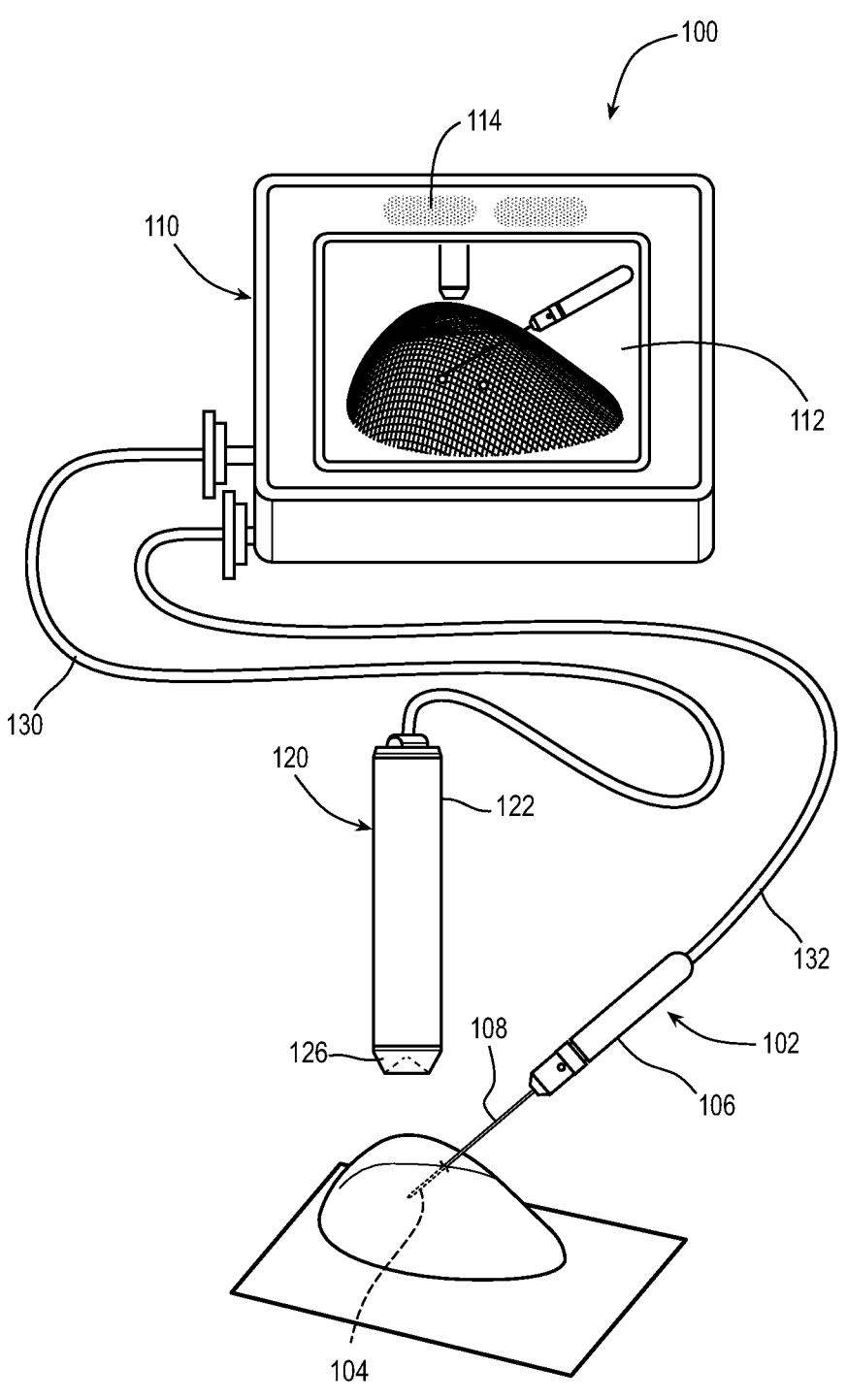
FIG. 1 shows show exemplary embodiments of a system for identifying a location of needle using actively modulated markers in accordance with some embodiments.

As shown in FIG. 1, the system 100 may include a needle 102, a controller 110, and a probe 120. The needle 102 and the probe 120 are coupled to the controller 110 using one or more cables 130, 132. The needle 102, controller 110, and probe 120 may be generally similar to embodiments described in U.S. Publication Nos. 2011/0021888, 2014/0309522, 2016/0354177, 2017/0252124, 2017/0319102, and 2018/0279907, U.S. application Ser. No. 16/124,053, and U.S. provisional application Ser. No. 62/871,059, the entire disclosures of which are expressly incorporated by reference herein.

The needle 102 may comprise a handle 106 and a shaft 108. The handle 106 may be held by a user and provide a coupling point for the cable 132. The shaft 108 may be configured for insertion into a patient. The shaft 108 may include one or more markers to reflect or transmit electromagnetic signals. In some embodiments, the body of the shaft 108 may be used to reflect or transmit electromagnetic signals. In some embodiments, antennas may be integrated one an insulation layer surrounding the shaft 108.

The probe 120 is a portable device having electromagnetic signal emitting and receiving capabilities. In some embodiments, the probe 120 is an elongate handheld device including a first or proximal end 122 which may be held by a user, and a second or distal end 124 intended to be placed against or adjacent tissue, e.g., a patient's skin or underlying tissue.

In some embodiments, the probe 120 includes one or more antennas, for receiving and transmitting mounted or carried on an antenna assembly 126. For example, in some embodiments, as shown in FIGS. 10A-10C, the one or more antennas may include one or more transmit antennas and receive antennas, as described further below. In some embodiments, the probe 120 may only have receive antennas and the needle 102 may comprise one or more transmit antennas. In some embodiments, the probe includes one antenna for receiving and transmitting mounted or carried on the antenna assembly 126.

The controller 110 may comprise one or more processors, a display 112, speakers 114, and other output devices. The processor may include one or more circuits, signal generators, gates, and the like (not shown) needed to generate signals for transmission by the transmit antenna(s) and/or to process signals received from the receive antenna(s). The components of the processor may include discrete components, solid state devices, programmable devices, software components, and the like, as desired.

The probe 120 may be coupled to a controller 110, e.g., by cables 130, for displaying information to a user of the probe 120, e.g., spatial or image data obtained via the antennas and/or other output from a digital signal processor. For example, the illustration shows an exemplary output that may be presented, including a three-dimensional model of the needle within the body region.

As shown, the internal components of the probe 120 may be provided in an outer housing or casing such that the probe 120 is self-contained, e.g., containing the components shown in FIGS. 9A-9D. For example, the casing may be relatively small and portable, e.g., such that the entire probe 120 may be held in a user's hand. Optionally, a portion of the probe 120 may be disposable, e.g., a portion adjacent the distal end 124, or a disposable cover, sleeve, and the like (not shown) may be provided if desired, such that at least a proximal portion of the probe 120 may be reusable. Alternatively, the entire probe 120 may be a disposable, single-use device while the controller 110 may be used during multiple procedures by connecting a new probe 120 to the controller 110, which may remain out of the surgical field yet remain accessible and/or visible, as desired. Additional information on construction and/or operation of the probe 120 may be found in the references incorporated by reference elsewhere herein.

Figure 2:
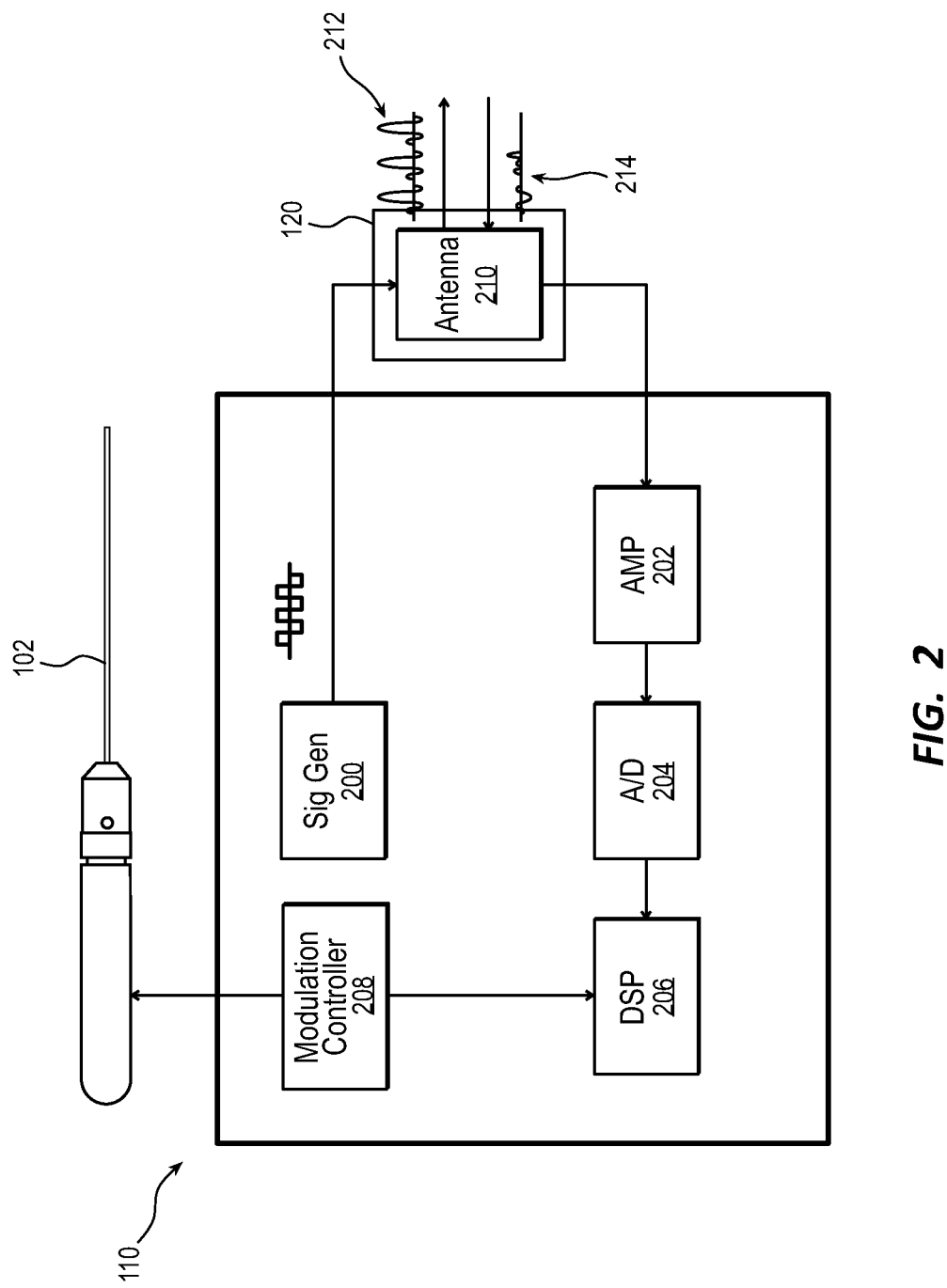
FIG. 2 is block diagram showing exemplary components of a controller according to a first embodiment.

FIG. 2 is block diagram showing exemplary components of a controller 110 according to a first embodiment (although, alternatively, some of the components may be located within the probe 120 or the needle 102). In the example shown, the controller 110 may include a signal generator 200, an amplifier 202, an analog-to-digital (A/D) converter 204, a modulation controller 208, and a digital signal processor (DSP) 206. The signal generator 200, e.g., a reference oscillator, produces an oscillating signal, such as a square wave signal, a triangular wave signal, or a sinusoidal signal.

For example, the controller 110 may include an impulse generator, e.g., a pulse generator and/or pseudo noise generator (not shown), coupled to the transmit antenna to generate transmit signals, and an impulse receiver for receiving signals detected by the receive antenna. The controller 110 may include a micro-controller and a range gate control that alternately activate the impulse generator and impulse receiver to transmit electromagnetic pulses, waves, or other signals via the transmit antenna, and then receive any reflected electromagnetic signals via the receive antenna, e.g., similar to other embodiments herein. Exemplary signals that may be used include microwave, radio waves, such as micro-impulse radar signals, e.g., in the ultrawide bandwidth region.

In the example shown in FIG. 2, a square wave signal may be sent from the signal generator 200 to the transmit antenna(s) of the antenna assembly 210 of the probe 120. The antenna assembly may include a transmit antenna and a receive antenna. In some embodiments, the antenna elements may include a bowtie transmit antenna and a bowtie receive antenna with the transmit antenna offset ninety degrees (90°) from the receive antenna to define a Maltese cross antenna.

When the square wave signal passes through the transmit antenna(s), the transmit antenna(s) may act as a band pass filter ("BPF") and convert the square wave signal to a series of pulses or other transmit signals 212. As such, the transmit signals transmitted by the probe 120 may include a series of pulses. Alternatively, the probe 120 may be configured to transmit continuous wave signals, e.g., similar to embodiments described in the references incorporated by reference herein. The transmit signal may be ultra-wideband (UWB) radar.

The transmit signals 212 may be transmitted into the tissue and reflected from the needle 102 or markers on the needle 102. The receive signals 214 are received by the antenna 210. Once the transmit signals 212 are reflected from the needle 102 or markers on the needle 102, the reflected signals (i.e., the receive signals 214) include a series of attenuated pulses.

The receive antenna(s) of the antenna assembly 210 of the probe 120 may receive the receive signals 214, which may be inputted into amplifier 202 in order to amplify the gain of the pulses. The output of the amplifier 202 may be inputted into an A/D converter 204 in order to convert the amplified analog signal into a digital signal. The digital signals output from the A/D converter 204 may be inputted into a DSP 206 for further processing. The DSP 206 may perform a number of processing functions including, but not limited to, calculating a difference in time from the time the transmit signals 212 were sent to the time the receive signals 214 were received (propagation time delay), determining the distance from the distal end of the probe 120 to the needle 102, determining the location of the tip of the needle 102 relative to the distal end of the probe 120, measuring the amplitude of the receive signals 214, and/or determining the direction of the needle 102 relative to the distal end of the probe 120.

As shown, a modulation controller 208 may be in communication with the needle 102 and the DSP 206. The modulation controller 208 may cause the needle 102 or needle markers to modulate the receive signals 214 in such a way that the DSP 206 may identify the reflected signals as being from the needle 102 or from a specific marker on the needle 102. The modulation controller 208 may send a signal that opens and closes a switch to cause the reflection properties of the needle 102 or needle markers to change, thereby modulating the reflected signals. The modulation may be used to better identify the needle or the needle markers and reduce noise.

Figure 3:
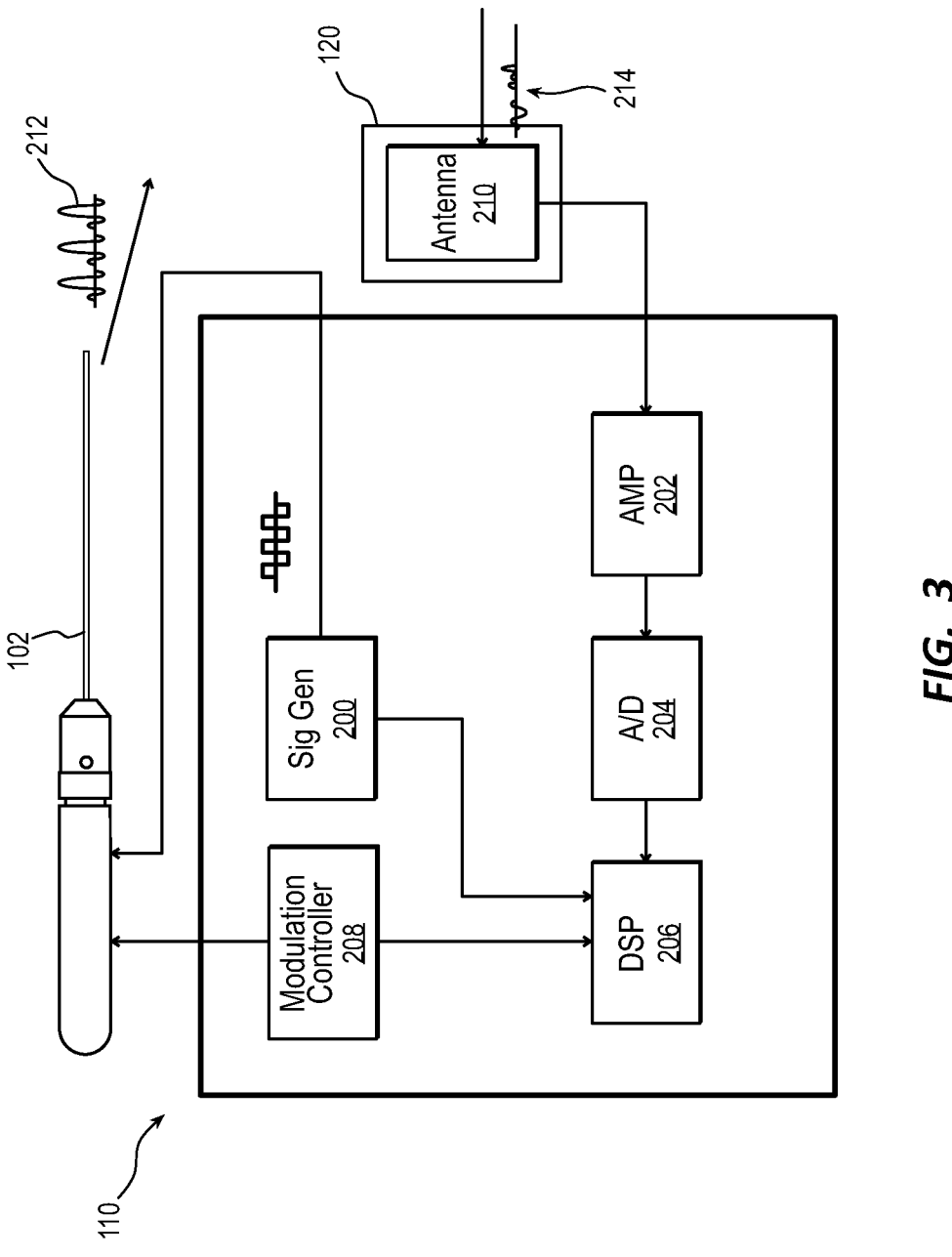
FIG. 3 is a block diagram showing exemplary components of a controller according to a second embodiment

FIG. 3 is a block diagram showing exemplary components of a controller 110 according to a second embodiment (although, alternatively, some of the components may be located within the probe 120 or the needle 102). As shown, the components of the embodiment in FIG. 3 may be the same as the components of the embodiment in FIG. 2. Accordingly, the description provided with reference to FIG. 2 may be applicable to FIG. 3.

The difference of the embodiment of FIG. 3 is that the square wave signal is sent from the signal generator 200 to the needle 102. The needle may include one or more transmit antenna(s). In some embodiments, the shaft or a portion of the shaft of the needle 102 may be used to transmit the transmit signals 212. In some embodiments, markers comprising antennas may be coupled to the needle 120 and used to transmit the transmit signals 212

The receive antenna(s) of the antenna assembly 210 of the probe 120 may receive the receive signals 214, which may be inputted into amplifier 202 in order to amplify the gain of the pulses. The output of the amplifier 202 may be inputted into an A/D converter 204 in order to convert the amplified analog signal into a digital signal. The digital signals output from the A/D converter 204 may be inputted into a DSP 206 for further processing. The DSP 206 may perform a number of processing functions including, but not limited to, calculating a difference in time from the time the transmit signals 212 were sent to the time the receive signals 214 were received (propagation time delay), determining the distance from the distal end of the probe 120 to the needle 102, determining the location of the tip of the needle 102 relative to the distal end of the probe 120, measuring the amplitude of the receive signals 214, and/or determining the direction of the needle 102 relative to the distal end of the probe 120.

As shown, a modulation controller 208 may be in communication with the needle 102 and the DSP 206. The modulation controller 208 may cause the needle 102 or needle markers to modulate the receive signals 214 in such a way that the DSP 206 may identify the reflected signals as being from the needle 102 or from a specific marker on the needle 102. The modulation controller 208 may send a signal that opens and closes a switch to cause the reflection properties of the needle 102 or needle markers to change, thereby modulating the reflected signals. The modulation may be used to better identify the needle or the needle markers and reduce noise.

Figure 4:
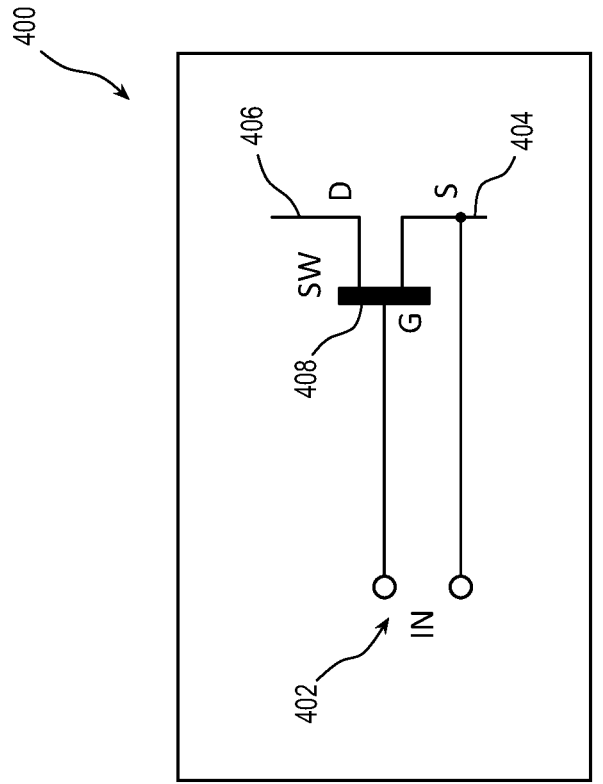
FIG. 4 is a schematic of a switch for the needle to modulate an electromagnetic signal.
Figure 5:
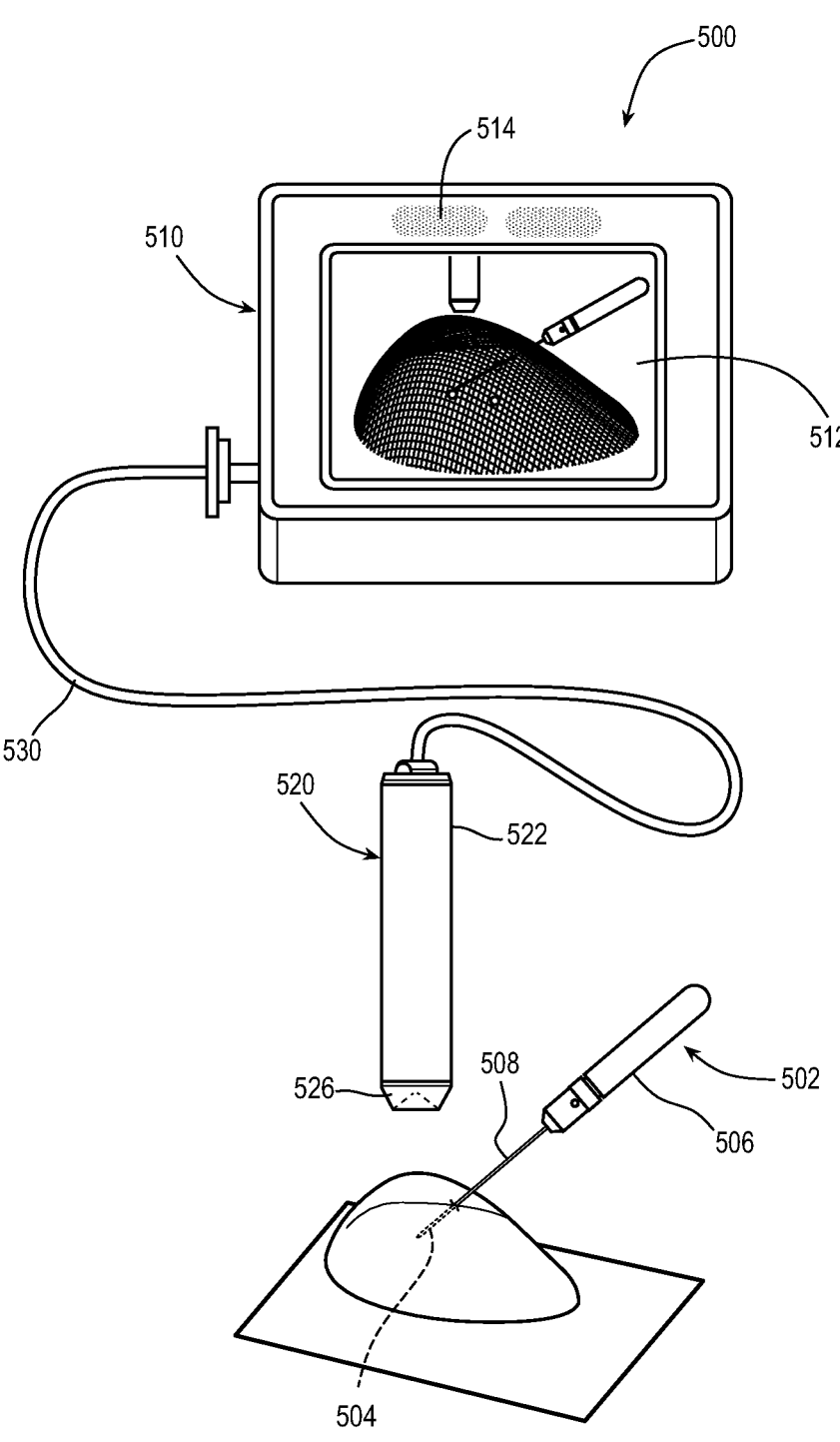
FIG. 5 shows exemplary embodiments of a system for identifying a location of a needle within a patient's body using passively modulated markers.

FIG. 4 is a schematic of a switch 400 for the needle 102 to modulate the electromagnetic signal. The switch 400 may be controlled by the controller 110 of FIGS. 1-3. For example, the modulation controller 208 of FIGS. 2 and 3 may send a signal to an input 402 of the switch to cause the switch 400 to open and close.

In the embodiment shown in FIG. 4, the switch 400 may be a field effect transistor (FET), e.g., a junction field effect transistor (JFET), with the modulation controller coupled to the gate (G) 408 and the other coupled to the source (S) 404. In an alternative embodiment, the switch 404 may be a Schottky diode In some embodiments, the source (S) 404 of the switch 400 may be electrically coupled to a first antenna and the drain (D) 406 may be coupled to a second antenna, such that the two antennas may become a combined antenna when the switch 400 closes. In some embodiments, the first antenna and the second antenna may be two separate portions of the needle shaft. In other embodiments, the antennas may be electrodes arranged on an insulation layer surrounding at least a portion of the needle shaft.

The modulation controller may provide a control signal that may open and close the switch 400, thereby connecting both wires 44 together. Thus, the result is that the switch 400 and antennas provide a tag that includes what equates to a high-frequency switch in the middle of the tag. By being able to change the switch 400 from closed to open, the reflection properties of the antenna provided by the antennas may be changed significantly. Specifically, the marker (i.e., switch and antennas) is made to periodically change its structure between two form factors. For example, as described further elsewhere herein, digital signal processing of the received signals using ultra-wideband (UWB) radar may use synchronous detection of the signal modulated with marker switching frequency. This significantly increases the signal-to-noise (SNR) on the marker signal because other contaminating signals remain unchanged within the modulation period.

In addition, the markers may include one or more features to facilitate identifying and/or distinguishing individual markers when multiple markers are implanted within a body region, e.g., to allow the probe to simultaneously or sequentially identify and localize each of the markers. For example, in one embodiment, a plurality of markers may be provided, with each marker controlled using a sequence generator of the controller or included in the marker to generate a code sequence to open and close the switch 400 to modulate signals reflected by the marker back to the probe based on the code sequence. The sequence generator of each marker may be pre-programmed such that the code sequences generated by the sequence generators are orthogonal to one another, i.e., the sequence generators may open and close the respective switches 400 to modulate the reflective properties of the markers differently from one another. The controller may be configured to analyze the reflected signals to identify and locate each of the markers substantially simultaneously based on the resulting modulation in the reflected signals received by the probe, e.g., as described in U.S. application Ser. No. 16/124,053 incorporated by reference herein.

FIGS. 5-8 show exemplary embodiments of a system 500 for identifying a location of a needle 502 within a patient's body using passively modulated markers (e.g., locating the position of the needle tip 504). In these embodiments, the passively modulated markers are indirectly controlled by a controller 510. For example, a signal reflected by or transmitted by the needle markers may modulated by an energy pulse (e.g., a light pulse) transmitted by the probe 520. Thus, the modulation may be controlled through light pulses rather than being directly wired to the controller 510. In an exemplary embodiment, the system 100 may be used to generate a three-dimensional model of a body region of a patient including a current position of the needle.

The system 150 may include a needle 502, a controller 510, and a probe 520. The probe 520 is coupled to the controller 510 using one or more cables 530. The needle 502, controller 510, and probe 520 may be generally similar to embodiments described in U.S. Publication Nos. 2011/0021888, 2014/0309522, 2016/0354177, 2017/0252124, 2017/0319102, and 2018/0279907, U.S. application Ser. No. 16/124,053, and U.S. provisional application Ser. No. 62/871,059.

The needle 502 may comprise a handle 506 and a shaft 508. The handle 506 may be held by a user. The shaft 508 may be configured for insertion into a patient. The shaft 508 may include one or more markers to reflect or transmit electromagnetic signals. In some embodiments, the body of the shaft 508 may be used to reflect or transmit electromagnetic signals. In some embodiments, antennas may be integrated one an insulation layer surrounding the shaft 508.

Figure 8:
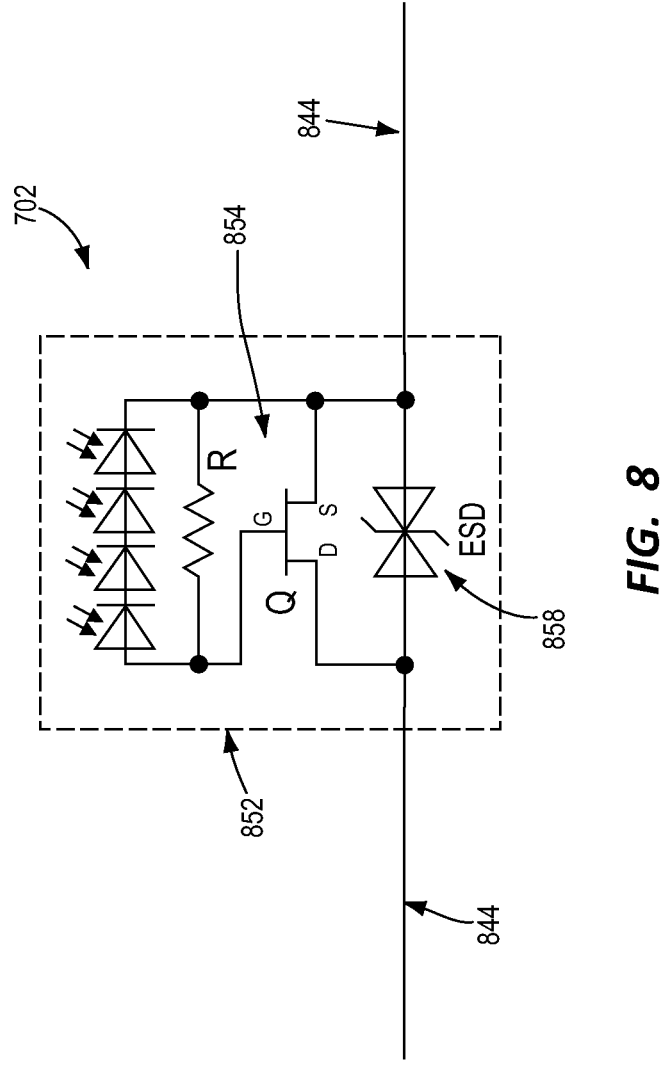
FIG. 8 is a schematic of a switch for the needle to modulate an electromagnetic signal.

The markers may include a voltage or power source or other power or energy converter, a switch that may be opened and closed when the energy converter generate electrical energy, and an Electro Static Discharge (ESD)

protection device (e.g., see FIG. 8). In some embodiments, the energy converter includes a plurality of photosensitive diodes capable of transforming incident light (e.g., infrared light) striking them into electrical energy (e.g., a predetermined minimum voltage). As shown, multiple pairs of diodes may be connected in series, which may be arranged orthogonally to one another spatially within the package. The package may be at least partially transparent or the diodes may be exposed such that light directed towards the package may be received by the diodes.

The probe 520 is a portable device having electromagnetic signal emitting and receiving capabilities. In some embodiments, the probe 520 is an elongate handheld device including a first or proximal end 522 which may be held by a user, and a second or distal end 524 intended to be placed against or adjacent tissue, e.g., a patient's skin or underlying tissue.

In some embodiments, the probe 520 includes one or more antennas, for receiving and transmitting mounted or carried on an antenna assembly 526. For example, in some embodiments, as shown in FIGS. 10A-10C, the one or more antennas may include one or more transmit antennas and receive antennas, as described further below. In some embodiments, the probe 520 may only have receive antennas and the needle 502 may comprise one or more transmit antennas. In some embodiments, the probe includes one antenna for receiving and transmitting mounted or carried on the antenna assembly 526.

Figure 7:
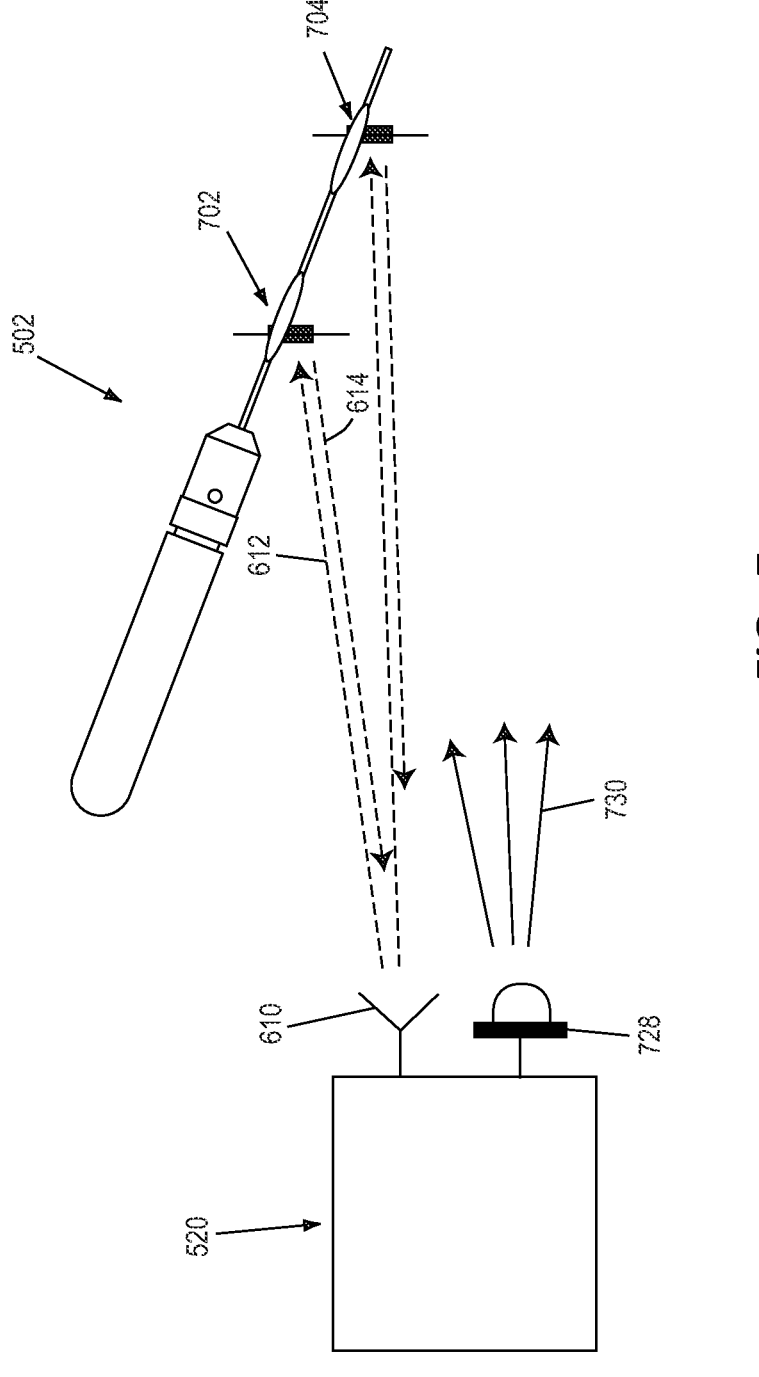
FIG. 7 is a simplified block diagram of a probe identifying and locating a needle using markers.

In addition, the probe 520 may include a light transmitter, e.g., a plurality of light fibers, configured to transmit light pulses into tissue contacted by the distal end (e.g., the plurality of light fibers 728 of FIG. 7). The light fibers may be coupled to a light source (not shown), such that light from the light source passes through the light fibers distally from the distal end of the probe 520.

In an exemplary embodiment, the light source is an infrared light source, e.g., capable of delivering near infrared light between, for example, eight hundred and nine hundred fifty nanometers (800-950 nm) wavelength. Optionally, the light fibers may include one or lenses, filters, and the like (not shown), if desired, for example, to focus the light transmitted by the probe 520 in a desired manner, e.g., in a relatively narrow beam extending to a wider angle beam, and the like. In another option, multiple light sources and/or filters may be provided to allow the probe 520 to deliver light pulses in different narrow bands. Alternatively, one or more light sources, e.g., IR LEDs, may be provided on the distal end instead of light fibers to deliver the light pulses.

The controller 510 may comprise one or more processors, a display 512, speakers 514, and other output devices. The processor may include one or more circuits, signal generators, gates, and the like (not shown) needed to generate signals for transmission by the transmit antenna(s) and/or to process signals received from the receive antenna(s). The components of the processor may include discrete components, solid state devices, programmable devices, software components, and the like, as desired.

The probe 520 may be coupled to a controller 510, e.g., by cables 530, for displaying information to a user of the probe 520, e.g., spatial or image data obtained via the antennas and/or other output from a digital signal processor. For example, the illustration shows an exemplary output that may be presented, including a three-dimensional model of the needle within the body region.

As shown, the internal components of the probe 520 may be provided in an outer housing or casing such that the probe 520 is self-contained, e.g., containing the components shown in FIGS. 9A-9D. For example, the casing may be relatively small and portable, e.g., such that the entire probe 520 may be held in a user's hand. Optionally, a portion of the probe 520 may be disposable, e.g., a portion adjacent the distal end 524, or a disposable cover, sleeve, and the like (not shown) may be provided if desired, such that at least a proximal portion of the probe 520 may be reusable. Alternatively, the entire probe 520 may be a disposable, single-use device while the controller 510 may be used during multiple procedures by connecting a new probe 520 to the controller 510, which may remain out of the surgical field yet remain accessible and/or visible, as desired. Additional information on construction and/or operation of the probe 520 may be found in the references incorporated by reference elsewhere herein.

Figure 6:
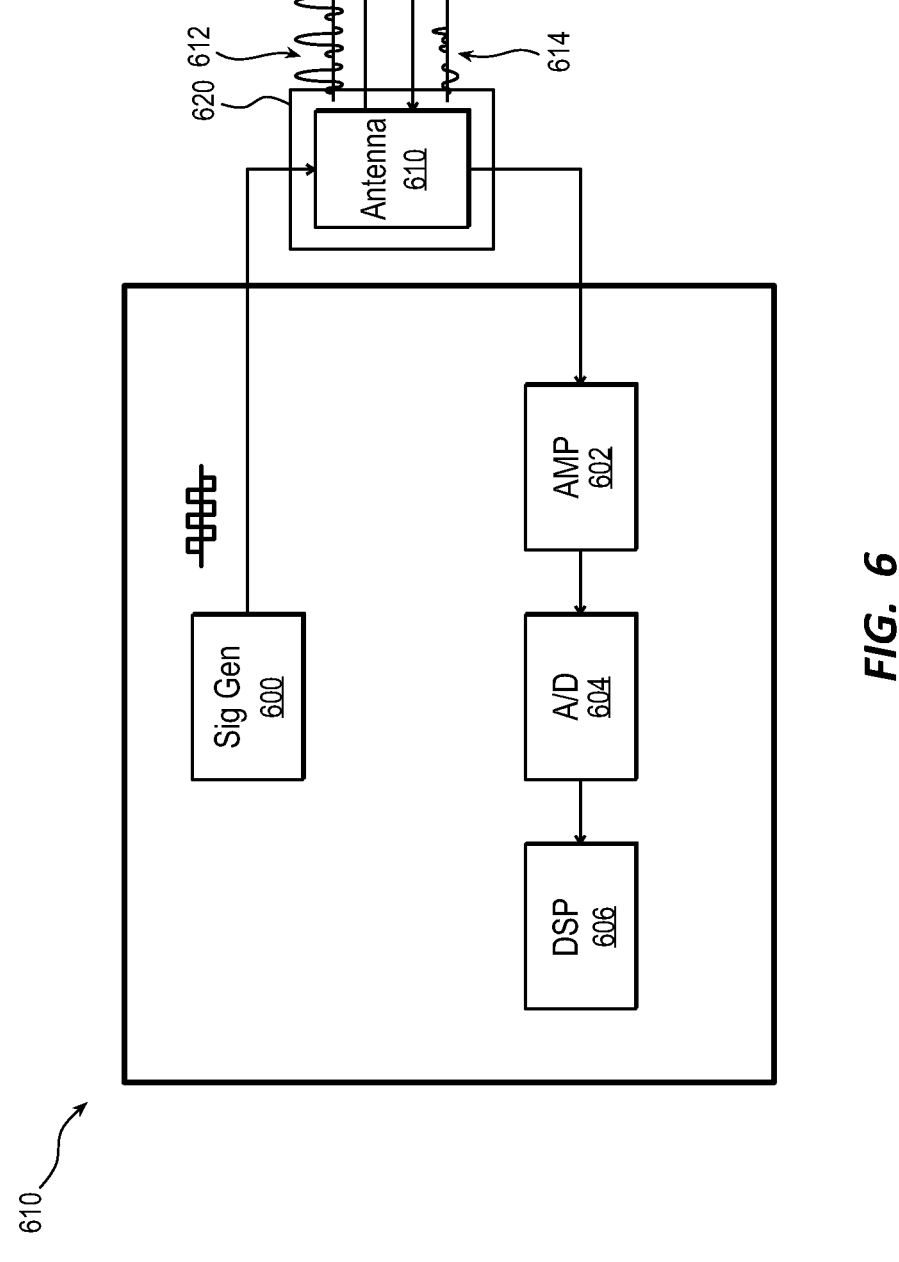
FIG. 6 is block diagram showing exemplary components of a controller 510 according to a first embodiment.

FIG. 6 is block diagram showing exemplary components of a controller 510 according to a first embodiment (although, alternatively, some of the components may be located within the probe 520 or the needle 502). In the example shown, the controller 510 may include a signal generator 600, an amplifier 602, an analog-to-digital (A/D) converter 604, a modulation controller 608, and a digital signal processor (DSP) 606. The signal generator 600, e.g., a reference oscillator, produces an oscillating signal, such as a square wave signal, a triangular wave signal, or a sinusoidal signal.

For example, the controller 510 may include an impulse generator, e.g., a pulse generator and/or pseudo noise generator (not shown), coupled to the transmit antenna to generate transmit signals, and an impulse receiver for receiving signals detected by the receive antenna. The controller 510 may include a micro-controller and a range gate control that alternately activate the impulse generator and impulse receiver to transmit electromagnetic pulses, waves, or other signals via the transmit antenna, and then receive any reflected electromagnetic signals via the receive antenna, e.g., similar to other embodiments herein. Exemplary signals that may be used include microwave, radio waves, such as micro-impulse radar signals, e.g., in the ultrawide bandwidth region.

In the example shown in FIG. 6, a square wave signal may be sent from the signal generator 600 to the transmit antenna(s) of the antenna assembly 610 of the probe 520. The antenna assembly may include a transmit antenna and a receive antenna. In some embodiments, the antenna elements may include a bowtie transmit antenna and a bowtie receive antenna with the transmit antenna offset ninety degrees (90°) from the receive antenna to define a Maltese cross antenna.

When the square wave signal passes through the transmit antenna(s), the transmit antenna(s) may act as a band pass filter ("BPF") and convert the square wave signal to a series of pulses or other transmit signals 612. As such, the transmit signals transmitted by the probe 520 may include a series of pulses. Alternatively, the probe 520 may be configured to transmit continuous wave signals, e.g., similar to embodiments described in the references incorporated by reference herein. In some embodiments, the transmit signal may be ultra-wideband (UWB) radar.

The transmit signals 612 may be transmitted into the tissue and reflected from the needle 502 or markers on the needle 502. The receive signals 614 are received by the antenna 610. Once the transmit signals 612 are reflected from the needle 502 or markers on the needle 502, the reflected signals (i.e., the receive signals 614) include a series of attenuated pulses.

The receive antenna(s) of the antenna assembly 610 of the probe 520 may receive the receive signals 614, which may be inputted into amplifier 602 in order to amplify the gain of the pulses. The output of the amplifier 602 may be inputted into an A/D converter 604 in order to convert the amplified analog signal into a digital signal. The digital signals output from the A/D converter 604 may be inputted into a DSP 606 for further processing. The DSP 606 may perform a number of processing functions including, but not limited to, calculating a difference in time from the time the transmit signals 612 were sent to the time the receive signals 614 were received (propagation time delay), determining the distance from the distal end of the probe 520 to the needle 502, determining the location of the tip of the needle 502 relative to the distal end of the probe 520, measuring the amplitude of the receive signals 614, and/or determining the direction of the needle 502 relative to the distal end of the probe 520.

FIG. 7 is a simplified block diagram of a probe 520 identifying and locating a needle using markers 702 and 704. In some embodiments, the probe 520 includes one or more antennas, for receiving and transmitting mounted or carried on an antenna assembly 610. For example, as shown in FIGS. 10A-10C, including one or more transmit antennas and receive antennas. In addition, the probe 520 may include a light transmitter, e.g., a plurality of light fibers 728, configured to transmit light pulses 730 into tissue contacted by the distal end of the probe 520. The light fibers 728 may be coupled to a light source (not shown), such that light from the light source passes through the light fibers 728 distally from the distal end of the probe 520.

In an exemplary embodiment, the light source is an infrared light source, e.g., capable of delivering near infrared light between, for example, eight hundred and nine hundred fifty nanometers (800-950 nm) wavelength. Optionally, the light fibers 728 may include one or lenses, filters, and the like (not shown), if desired, for example, to focus the light transmitted by the probe 520 in a desired manner, e.g., in a relatively narrow beam extending substantially parallel to the longitudinal axis, in a wider angle beam, and the like. In another option, multiple light sources and/or filters may be provided to allow the probe 520 to deliver light pulses in different narrow bands. Alternatively, one or more light sources, e.g., IR LEDs, may be provided on the probe 520 instead of light fibers 728 to deliver the light pulses 730.

The transmit signals 612 transmitted by the probe 520 may include a series of pulses. Alternatively, the probe 520 may be configured to transmit continuous wave signals, e.g., similar to embodiments described in the references incorporated by reference herein. The transmit signals 612 may be transmitted into the tissue and reflected from the marker(s) 702 and 704 along the needle 502, as represented by the receive signals 614. Once the transmit signals 612 are reflected from the marker(s) 702 and 704, the reflected signals (i.e., the receive signals 614) may include a series of attenuated pulses (shown in FIG. 6).

With additional reference to FIG. 8, the marker(s) 702 and 704 may include one or more circuits or other electrical components encased or embedded in an electronics package and configured to modulate incident signals from the probe 520. In an exemplary embodiment, a semiconductor chip, print circuit board (PCB), and/or other circuit may be carried in the package that includes a voltage or power source or other power or energy converter 852, a switch 854 that may be opened and closed when the energy converter 852 generate electrical energy, and an ESD protection device 858.

In the embodiment shown in, the switch 854 may be a field effect transistor (FET), e.g., a junction field effect transistor (JFET), with one end of the diodes 852 coupled to the gate (G) and the other coupled to the source (S), with a resistor 56 coupled between the gate (G) and the source (S), e.g., to discharge the diodes 852 when there is no IR light. As shown, in some embodiments, the energy converter 852 may be a series of diodes. Light intermittently striking the diodes may generate a voltage across the gate (G) and source (S) of the switch 854 to provide a control signal that may open and close the switch 854. For example, the switch 854 may be in the open configuration when infrared light is absent, and in the closed configuration when infrared light strikes the diodes. When in a closed position the switch 854 may connect two antennas, electrodes, wires, or portions of the needle shaft. Thus, the result is that the marker 740 provides a passive tag that includes what equates to a high-frequency switch in the middle of the marker 740. By being able to change the switch 854 from closed to open, the reflection properties of the antenna provided by the reflectors 854 may be changed significantly.

Specifically, the marker 702 is made to periodically change its structure between two form factors. For example, digital signal processing of the received signals using ultra-wideband (UWB) radar may use synchronous detection of the signal modulated with marker switching frequency. This significantly increases the signal-to-noise (SNR) on the marker signal because other contaminating signals remain unchanged within the modulation period. To provide a mechanism for a synchronous detector, the marker switching process may be controlled by the probe 520 by illuminating breast tissue with near infrared (IR) light pulses that are received by the marker 704.

Switching of the marker reflective form-factor is controlled with a set of diodes operating in photovoltaic mode. When the diodes receive light from the probe 520 (represented by arrows 730 in FIG. 7), the diodes generate voltage that is applied between the gate (G) and source (S) of the switch 854, which closes and connects together the drain (D) and source (S) making both antennas connected together. When the light is off, the switch 854 is open and the drain (D) and source (S) are electrically disconnected.

In addition, the markers may include one or more features to facilitate identifying and/or distinguishing individual markers when multiple markers are implanted within a body region, e.g., to allow the probe 520 to simultaneously or sequentially identify and localize each of the markers. For example, in one embodiment, a plurality of markers may be provided, with each marker including a clock circuit or block (not shown) coupled to the diodes and a sequence generator (also not shown) coupled to the clock circuit and the switch 854 to generate a code sequence to open and close the switch 854 to modulate signals reflected by the marker 704 back to the probe 520 based on the code sequence. The sequence generator of each marker 704 may be pre-programmed such that the code sequences generated by the sequence generators are orthogonal to one another, i.e., the sequence generators may open and close the respective switches 854, based on the light pulses from the light source 728 of the probe 520, to modulate the reflective properties of the markers differently from one another. The probe 520 may be configured to analyze the reflected signals to identify and locate each of the markers substantially simultaneously based on the resulting modulation in the reflected signals received by the probe 520, e.g., as described in U.S. application Ser. No. 16/124,053 incorporated by reference herein.

In addition or alternatively, the package and/or the diodes may include one or more coatings and/or filters, e.g., to allow the probe 520 to communicate individually, e.g., sequentially, within individual markers, similar to markers disclosed in U.S. Publication Nos. 2017/0252124 and 2017/0319102, incorporated by reference herein. For example, the probe 520 may be capable of delivering separate narrow bands of infrared light and the markers may include filters (not shown) such that individual markers may only receive respective narrow bands, thereby allowing the probe 520 to modulate and identify, individual markers. Alternatively, the markers may include processors (not shown) that analyze light pulses from the probe 520 such that the processors may identify commands from the probe 520, e.g., to modulate individual markers. In this manner, the probe 520 may be able to activate and/or modulate individual markers such that the probe 520 may identify and/or locate the markers sequentially by sending commands in the light pulses to activate individual markers in a desired sequence, e.g., as described in the references incorporated by reference herein.

Turning to FIGS. 9A-9D, exemplary internal components of a probe are shown (after removing the outer housing 21), e.g., including an internal sleeve or housing carrying the antenna assembly, and, optionally, shielding, on or within its distal end. The internal components of the probe may be used for the probe 120 shown in FIGS. 1-3 or the probe 520 FIGS. 5-7. While the internal components of the probe are shown with a light source 28, the probe 120 shown in FIGS. 1-3 may not include such a light source. With particular reference to FIG. 9D, the antenna assembly 30 includes a base 32 including a substantially planar distal surface 32a, e.g., extending perpendicular to longitudinal axis 25, and a plurality of proximal planar surfaces 32b including antenna elements 32T, 32R. Alternatively, a single proximal planar surface (not shown) may be provided opposite the distal surface 32a including antenna elements.

The distal surface 32a may be located at a distal-most location of the distal end 24 of the probe 20, e.g., such that the distal surface 32a may be placed directly against a body surface, e.g., a patient's skin, tissue surface, and the like (e.g., covered with a thin membrane or cover to prevent fluids from entering the probe and/or other contamination). The base 32 may be formed from ceramic and/or other nonconductive material, e.g., having desired dielectric properties. For example, the base 32 may be formed from material having a dielectric constant (permittivity) similar to the tissue type the probe is intended to be used with, e.g., a dielectric constant similar to human breast tissue, skin, muscle, bone, fat or other tissue.

In the configuration shown in FIG. 9D, the antenna elements may include a pair of transmit antennas 32T and a pair receive antennas 32R arranged in bowtie configurations on the proximal surfaces 32b of the base 32, e.g., with the transmit antennas 32T offset ninety degrees (90°) from the receive antennas 32R to define a Maltese cross antenna. Each of the antenna elements 32T, 32R may be formed separately and then attached to the corresponding proximal surfaces 32b or may be deposited directly onto the proximal surfaces 32b. In an exemplary embodiment, the antenna elements 32T, 32R may be formed from silver film or other material deposited onto the proximal surfaces 32b of the base 32.

Circuitry 35, e.g., a printed circuit board, flex circuit, and the like, may be coupled to the antennas 32T, 32R, e.g., including a PCB on which are provided one or more transformers and/or connectors (not shown) coupled to the respective antenna elements 32T, 32R by appropriate leads 35a. As shown in FIGS. 9A and 9B, coaxial cables or other leads 35b may be coupled to connectors on the PCB to allow the antenna elements 32T, 32R to be coupled to other components of the system, e.g., to cause the antenna elements 32T to transmit signals and/or to communicate received signals to other components of the system, similar to other embodiments described herein.

As shown in FIGS. 9C and 9D, the base 32 also includes a plurality of radial slots 33, e.g., a slot 33 between adjacent planar surfaces 32b. The slots 33 may extend axially from the distal surface 32a to the proximal surfaces 32b to substantially isolate the antenna elements 32T, 32R from one another by air within the slots 33, which may increase sensitivity, reduce crosstalk and/or other noise, and the like. Alternatively, the slots 33 may be filled with other insulating material, e.g., foam and the like (not shown), which may have a desired relatively low dielectric constant to substantially isolate the antenna elements 32T, 32R from one another. In addition, as shown in FIG. 9C, one or more light fibers or other light sources 28 may be positioned within one or more of the slots 33, e.g., to deliver light pulses beyond the distal surface 32a of the base 32, as described elsewhere herein.

Optionally, as shown in FIGS. 9A and 9B, the base 32 may be mounted within shielding 37, which may in turn, be coupled to the distal end 26b of the inner housing 26 (and/or the distal end 24 of the outer housing 21), e.g., by one or more of bonding with adhesive, sonic welding, fusing, cooperating connectors (not shown), and the like, similar to embodiments in the references incorporated by reference herein. The shielding 37 may have a length (i.e., along the axis 25) substantially longer than a thickness of the base 32 (i.e., the distance along the axis 25 from the distal surface 32a to a proximal end of the base 32). The distal surface 32a of the base 32 may be substantially flush with the distal end of the shielding 37 such that the distal surface 32a may contact tissue during use, as described elsewhere herein. Optionally, a Mylar film or other relatively thin layer of material (not shown) may be provided over the distal surface 32a of the base 32 and/or the shielding 37, e.g., to prevent fluids or other material entering the tip, reduce contamination, and/or otherwise protect the tip of the probe 20.

With continued reference to FIGS. 9A-9D, the proximal surfaces 32b of the base 32 may be exposed to a region of air within the shielding 37. Because of the low dielectric constant of air (e.g., close to one (1)), the air provides a dielectric or impedance mismatch with the material of the base such the transmission from the transmit antenna 32T is focused distally, i.e., towards the tissue contacted by the base 32. With the material of the base 32 chosen to substantially match the dielectric constant of tissue, the depth of transmission into the tissue may be enhanced. The air behind the base 32 may minimize lost energy that would otherwise be emitted by the transmit antenna 32T away from the tissue. The air behind the base 32 within the shielding 37 may also minimize crosstalk, noise and/or may otherwise enhance operation of the probe 20.

The transmit and receive antennas may be positioned in numerous ways. FIGS. 10A-10C illustrate different potential arrangements of the antennas of the probe. For simplicity, the probe 120 in FIG. 10A-10C is labeled according to the probe in FIG. 1. However, the following may also be applicable to embodiments of the probe 520 of FIG. 5. In the embodiment shown in FIG. 10A, the probe 120 includes a transmit antenna 132T located at the center of the substrate 132 and three orthogonally oriented receive antennas 132R positioned evenly around the transmit antenna 132T. Alternatively, as shown in FIG. 10B, a receive antenna 132R' may be mounted at the center with the transmit antenna 132T' with three additional receive antennas 132R' positioned evenly around the central antenna. In a further alternative, shown in FIG. 10C, the probe 120" may include a transmit antenna 132T" located at the center of the substrate 132 "and four orthogonally oriented receive antennas 132R" positioned evenly around the transmit antenna 132T." It will be appreciated that other arrangements may be provided, e.g., including at least two receive antennas spaced apart from one another to provide different propagation time delays and resulting distance measurements to each marker being localized.

In some embodiments, the probe 120 includes a single transmit antenna 132T, e.g., including a pair of bowtie antenna elements, on the proximal surface 132b of the substrate 132, a plurality of receive antennas 132R, each including a pair of bowtie antenna elements, spaced apart from one another on the proximal surface 132b of the substrate 132. Thus, the transmit antenna 132T may be configured for transmitting electromagnetic signals, e.g., ultra-wide band radar signals, into a patient's body along with pulsed light from the light source 128 to cause a switch (not shown) of each marker to open and close to modulate reflected signals from each marker. Each receive antenna 132R may be configured for receiving reflected signals from the patient's body independent of the others, and a processor of the probe 120 may process the modulated reflected signals to identify and/or locate each marker, e.g., to determine a distance from each marker to the respective receive antennas 132R.

Given that the receive antennas 132R are spaced apart from one another, the distance from each receive antenna 132R to each marker is different and, consequently, the propagation time delay from the transmit signals to the time the receive signals are received by each receive antenna 132R will be different. The processor may use the differences in the time delay and resulting distance dimension to perform trilateration and determine the spatial relationship of each marker relative to the distal end of the probe, e.g., to determine an x-y-z coordinate location of each marker. This spatial relationship may be mapped to a model generated by the system, e.g., similar to other embodiments herein, to allow a surgeon or other user to observe the location of the marker(s) relative to the body region using the model (including representations of each marker) presented on a display.

If multiple markers are spaced along the length of the needle, the processor may identify and/or localize each marker simultaneously, e.g., using orthogonal code sequences, or sequentially, e.g., using filters and/or bit commands, similar to other embodiments herein. Alternatively, the probe 120 may be used to identify and localize a single marker at the tip of a needle and provide a three-dimensional coordinate for the marker, which may be incorporated into any of the models described herein.

For example, initially, the distal end of the probe may be placed against the patient's skin (or other surface) and the probe may be activated. In some embodiments as described elsewhere herein, signals from the antenna(s) of the probe may be delivered along with pulsed light from the light source to cause the switches to open and close as the markers receive and reflect signals back to the probe. In other embodiments, signals from the antenna(s) of the probe may be delivered along with input signals directly sent to the switches to open and close. The reflected signals from the two states (switches open and closed) may be subtracted from one another, substantially eliminated other noise, and allowing the probe to identify and/or locate the markers. The probe may acquire signals from the markers substantially simultaneously, e.g., using orthogonal code sequences, or sequentially by activating and/or polling the markers sequentially, as described elsewhere herein and in the references incorporated by reference herein.

The processor of the probe or controller may then identify and/or localize the markers based at least in part on the reflected signals. For example, based on propagation time delay between the transmitted signals and received reflected signals, distances may be determined from the markers to the distal end, e.g., substantially simultaneously or sequentially, thereby providing distances from the markers to the distal end (and consequently to the first surface location on the breast, as described further below). Optionally, the display may present information to the user related to the location of the markers relative to the probe based on the current location of the distal end. In some embodiments the display may include a readout on a portion thereof providing distances from each of the markers to the distal end of the probe. The distance information may be displayed as a numerical value representing the distance in units of length, such as in inches (in.) or centimeters (cm).

Based on at least some of the distance information, the processor of the probe or controller may obtain a reference frame, e.g., a three-dimensional x-y-z or other orthogonal reference frame, based on the locations of the markers within the breast. Thus, the reference frame may be fixed relative to the breast and its associated structures, e.g., the overlying skin.

Once the reference frame is established, the processor may generate the model, e.g., by using trilateration, i.e., the distances from the markers to the respective surface locations where the distances were acquired. This process may be repeated for multiple surface locations to identify multiple locations of the patient's skin. Once sufficient samples have been taken, the processor may predict the surface of the breast and present the resulting model on a display. The number of samples to generate the model may be based the size of the surface of the body region, e.g., breast, and/or the desired granularity of the model to be displayed.

Once the model has been constructed, the processor may identify the current location of the distal end of the probe at any time and then add a representation of the probe and the needle to the model. Using this presentation, the surgeon may be able to observe in real time the location of the probe relative to the markers along the needle. In some embodiments, the processor may also calculate and display the location of the tip of the needle based on the location of the markers. In some embodiments, the entire length of the needle may be displayed on the model.

Calculations of the markers and probe locations from distance measurements may be performed using known methods of computational geometry and geometry algebra dealing with distance geometry problems. Various methods for solving distance geometry problems have been developed for visualization of graphs given by set of nodes and lengths of edges connecting them. Such types of problems frequently occur in presentation and analysis of network structures, in molecular physics, robotics and other fields (see, for example a review by L. Liberti et al "Euclidian Distance Geometry and Applications" *SIAM Review*, 2014, Vol. 56, No 1, pp. 3-69, the entire disclosure of which is expressly incorporated by reference herein). Many different methods developed for distance geometry problems may be applicable to the systems and method herein. For example, those disclosed U.S. application Ser. No. 17/089,440, incorporated by reference herein.

FIGS. 11-19 illustrate embodiments of needles that may be used with the systems and probes of FIGS. 1-10. The needle shafts of the embodiments may be attached to a handle and be configured to be inserted into a body of a patient. The needle shafts comprise a lumen formed from a hollow bore of the needle shaft. The needle may be used for a variety of tasks. For example, the lumen may be used to introduce administer medicine, introduce additional medical equipment, withdraw samples of tissue, or withdraw bodily fluids. For instance, tissue markers designating an ablation area may be introduced using the needle 1100. In some embodiments, an ablation device may be introduced into a patient via the needle 1100.

FIGS. 11-12 illustrate a first embodiment of a needle 1100 that may be used with the systems and probes of FIGS. 1-10. More specifically, FIG. 11 illustrates an assembled needle shaft 1120 and FIG. 12 is an exploded view of the needle shaft 1120. The needle comprises three portions: a distal portion 1124, an intermediate portion 1112, and a proximal portion 1122.

The distal portion 1124 may be beveled to form a point to introduce the needle 1100 into a patient. The distal portion 1124 comprises a conductive material. For example, the distal portion 1124 may be made of stainless steel or carbon steel.

The proximal portion 1122 may be coupled to a handle of the needle 1100. The proximal portion 1122 may comprise a conductive material. For example, the proximal portion 1122 may be made of stainless steel or carbon steel. The conductive material of the proximal portion 1122 may be the same or different than the distal portion 1124.

The intermediate portion 1112 between the distal portion 1124 and the proximal portion 1122. The intermediate portion 1112 may comprise a joint 1112 and an electronics package 1102. The joint 1112 may be a rigid cylinder configured to physically couple to the distal portion 1124 and the proximal portion 1122. As shown in FIG. 12, the intermediate portion 1102 may include a first socket 1202 and a second socket 1204. The first socket 1202 may receive and secure the distal portion 1124. The second socket 1204 may receive and secure the proximal portion 1122. The first socket 1202 and the second socket 1204 may couple to the distal portion 1124 and the proximal portion 1122 using any suitable technique, such as friction fit, solvent bonding, gluing, welding, over molding, etc. In some embodiments, the first socket 1202 and the second socket 1204 may include internal threads that threadingly engage with threads on the distal portion 1124 and the proximal portion 1122.

The joint 1112 may be a non-conductive material such as a plastic. The joint 1112 may provide an electrical buffer between the distal portion 1124 and the proximal portion 1122 such that the distal portion 1124 is physical coupled while being electrically disconnected from the proximal portion 1122. As illustrated in FIG. 12, the joint 1112 may include a buffer 1206 that separates the first socket 1202 and the second socket 1204 where the distal portion 1124 and the proximal portion 1122 are secured.

The electronics package 1102 may be integrated with the joint 112. For example, the electronics package 1102 may be positioned on the exterior of the joint 1112 and curved to follow the curvature of the joint 112. In some embodiments, the electronics package 1102 may be integrated within the joint 1112. In some embodiments, the joint 1112 may comprise a clear plastic to allow light to penetrate to an electronics package integrated within the joint 1112.

The illustrated electronics package 1102 features a passive switch powered through light pulses as discussed with reference to FIGS. 5-8. In some embodiments, the electronics package 1102 may include one or more circuits 1114 or other electrical components encased or embedded in the electronics package 1102 and configured to modulate incident signals from a probe. In some embodiments, a semiconductor chip, print circuit board (PCB), and/or other circuit may be carried in the package that includes a voltage or power source or other power or energy converter, a switch that may be opened and closed when the energy converter generate electrical energy, and an Electro Static Discharge (ESD) protection device.

While the illustrated embodiment includes a switch that may be powered using light pulses and an energy converter it is also contemplated that in some embodiments, the switch of the electronics package may be hardwired to the controller as discussed with reference to FIGS. 1-4 and actively controlled in order to modulate the signal.

The electronics package 1102 may be electrically coupled to the distal portion 1124 and the proximal portion 1122. A first lead 1106 and a first electrode 1110 may couple a switch of the electronics package 1102 to the distal portion 1124. A second lead 1104 and a second electrode 1108 may couple the switch of the electronics package 1102 to the proximal portion 1122. The distal portion 1124 and the proximal portion 1122 may be coupled to the switch such that when the switch is opened the distal portion 1124 and the proximal portion 1122 are electrically disconnected, and when the switch is closed the distal portion 1124 and the proximal portion 1122 are electrically connected.

In the illustrated embodiment, the needle shaft 1120 is used as a marker. The distal portion 1124 and proximal portion 1122 function as reflectors for the marker. The electronics package 1102 provides a switch configured to open and close. Opening and closing the switch electrically connects and disconnects the distal portion 1124 and the proximal portion 1122 and modulates electromagnetic signals transmitted by a probe and reflected by the distal portion 1124 and the proximal portion 1122. In some embodiments, an insulation layer may be added to a portion of the distal portion 1124, the proximal portion 1122, or both to configure the reflective properties of the needle shaft 1120.

In some embodiments, the needle shaft 1120 may be used to transmit a signal rather than reflect a signal. For example, a signal may be generated by a controller and conducted down the proximal portion 1122. The proximal portion 1122 may transmit the signal. Further, when the switch changes to a closed position, the transmission may be altered as the signal is now transmitted along the proximal portion 1122 and the distal portion 1124. Thus, the switch opening and closing may modulate a signal transmitted from the needle shaft 1120.

While the illustrated embodiment shows only one electronics package 1102, the needle shaft 1120 may be further segmented to create additional markers along the needle 1100.

FIGS. 13 and 14 demonstrate how a system 1300 may determine a location of a needle tip 1314. More specifically, FIG. 13 illustrates a simplified block diagram of a system 1300 for localization of a needle tip 1314 using two markers (i.e., first marker 1316 and second marker 1318) along the length of a needle 1310. Further, FIG. 14 is a cross-sectional view of the needle 1310 that illustrates a relationship between the markers (i.e., first marker 1316 and second marker 1318) and the needle tip 1314 that may be used by the system 1300 to determine the location of the needle tip.

The embodiment illustrated in FIGS. 13-14 uses actively modulated markers as described with reference to FIGS. 1-4.

That is, the first marker 1316 and the second marker 1318 are markers are directly controlled by a controller (e.g., UWB radar console and modulation controller 1302). While the illustrated embodiment includes actively modulated markers, the process to determine the location of the needle tip 1314 may be used by systems using passively modulated markers (e.g., FIGS. 5-8).

The UWB radar console and modulation controller 1302 may control the antenna module 1304 and the reflector module 1306. The UWB radar console and modulation controller 1306 may be part of or all of the controller 110 shown in FIG. 1 or the controller 510 shown in FIG. 5. Accordingly, disclosure related to the UWB radar console and modulation controller 1302, the controller 110, and the controller 510 may be applicable to the various embodiments. The UWB radar console and modulation controller 1302 may comprise a processor and memory to perform the actions described herein.

The UWB radar console and modulation controller 1302 may generate or cause the antenna module 1304 to generate an UWB radar signal. The antenna module 1304 may be a device that includes a transmit antenna 1332 and receive antennas 1330a-1330d (herein receive antennas 1330). For example, the antenna module 1304 may be any of the probes described with reference to the previous figures. The antenna module 1304 may transmit the UWB radar signal into a patient, and receive reflected signals from the markers (e.g., first marker 1316 and second marker 1318) of the needle 1310. The antenna module 1304 may send the reflected signals to the UWB radar console and modulation controller 1302.

The UWB radar console and modulation controller 1302 may also control the reflector module 1306. The reflector module 1306 may control the switching sequence of the markers on the needle 1310 to control modulation of the reflected signal. The UWB radar console and modulation controller 1302 may send a signal to reflector module 1306 to configure the reflector module 1306 to provide a specific modulation sequence for each marker. The reflector module 1306 may comprise circuitry and processors to receive a signal from the UWB radar console and modulation controller 1302 and generate an input signal to the switches of the reflectors. In some embodiments, the reflector module 1306 may cause the markers to operate using orthogonal modulation codes such that the UWB radar console and modulation controller 1302 may distinguish the markers enable the UWB radar console and modulation controller 1302 to evaluate the distances to the markers from multiple locations substantially simultaneously.

The needle 1310 includes a needle shaft 1312 and a needle tip 1314. In some embodiments, the reflector module 1306 may be incorporated in the handle of the needle. In other embodiments, the reflector module 1306 may be a standalone device. In yet other embodiments, the reflector module 1306 may be combined with a controller such as the UWB radar console and modulation controller 1302, the controller 110 shown in FIG. 1, or the controller 510 shown in FIG. 5.

The needle 1310 may include a set of markers (e.g., first marker 1316 and second marker 1318) along the length of the shaft 1312. The UWB radar console and modulation controller 1302 may use the reflected to identify and/or localize the markers based at least in part on the reflected signals. For example, based on propagation time delay between the transmitted signals and received reflected signals, distances between the antenna module 1304 and the markers may be determined. Given that the receive antennas 1330 are spaced apart from one another, the distance from each receive antenna to each marker is different and, consequently, the propagation time delay from the transmit signals to the time the receive signals are received by each receive antenna will be different. The UWB radar console and modulation controller 1302 may use the differences in the time delay and resulting distance dimension to perform trilateration and determine the spatial relationship of each marker relative to the distal end of the antenna module 1304 to determine an x-y-z coordinate locations (e.g., first location 1322, second location 1320) of each marker. This spatial relationship may be mapped to a model generated by the system. In other embodiments, a single receive antenna may be used to capture measurements at multiple points to perform trilateration.

The UWB radar console and modulation controller 1302 may use the coordinate locations of the markers to determine the needle tip coordinates 1324. For example, determining the locations of the first marker 1316 and the second marker 1316, the UWB radar console and modulation controller 1302 can compute the coordinates of the needle tip ($x_T$, $y_T$, $z_T$) using a known length between the needle tip 1314 and the center of the first marker 1316 (i.e., L1 1404) and a known length between the first marker 1316 and the second marker 1318 (i.e., L2 1402). For example, the UWB radar console and modulation controller 1302 may use the following equations:

$$x_T = x_1 - \frac{L1(x_2 - x_1)}{L2}$$

where:
  $X_T$ is the x-coordinate of the needle tip
  $X_1$ is the x-coordinate of the first marker
  $X_2$ is the x-coordinate of the second marker
  L1 is the length between the needle tip and the center of the first marker
  L2 is the length between the first marker and the second marker $$y_T = y_1 - \frac{L1(y_2 - y_1)}{L2}$$

where:
  $y_T$ is the y-coordinate of the needle tip
  $y_1$ is the y-coordinate of the first marker
  $y_2$ z is the y-coordinate of the second marker $$z_T = z_1 - \frac{L1(z_2 - z_1)}{L2}$$

where:
  $z_T$ is the z-coordinate of the needle tip
  $z_1$ is the z-coordinate of the first marker
  $z_2$ is the z-coordinate of the second marker FIGS. 15-19C illustrate embodiments of a needle comprising markers with reflectors integrated exterior of an insulation layer surrounding a needle shaft.

More specifically, FIGS. 15-16C illustrate a needle 1500 with markers comprising a pair of cylindrical electrodes. The illustrated embodiment of the needle 1500 uses actively modulated markers and may be used by the systems discussed in relation to FIGS. 1-4 and FIGS. 13-14. However, it is also contemplated that the actively modulated markers may be replaced with passively modulated markers such as discussed with reference to FIGS. 5-8.

As shown in FIG. 15, the needle 1500 may comprise a shaft 1502 with a first marker 1520 and a second marker 1510. The first marker 1520 may be positioned at a first location closer to a proximal end of the needle 1500 and the second marker 1510 may be positioned at a second location closer to a tip of the needle 1500.

The first marker 1520 and the second marker 1510 may reflect signals transmitted by a probe. The first marker 1520 is formed by a pair of electrodes (i.e., first electrode 1524 and second electrode 1526) coupled with a first switch 1522 via a pair of leads 1528a and 1528b. The second marker 1510 is also formed by a pair of electrodes (i.e., third electrode 1514 and fourth electrode 1516) coupled with a second switch 1512 via a pair of leads 1518a and 1518b. The first switch 1522 and the second switch 1512 may be located on opposite sides of the shaft 1502 (e.g., the first switch 1522 may be on the right side of the shaft 1502 and the second switch 1512 may be on the right side of the shaft 1503).

The electrodes (i.e., first electrode 1524, second electrode 1526, third electrode 1514, and fourth electrode 1516) may comprise conductive material in a cylindrical shape. Each of the electrodes are spaced along a length of the needle shaft 1502 with a switch between each pair of electrodes. In the illustrated embodiment, the electrodes entirely wrap around the circumference of the shaft 1502. In other embodiments, the electrodes may only wrap around a portion of the circumference of the shaft 1502.

When the needle 1500 is inserted into the patient, each of the electrodes are electrically connected to the tissue. The switches (e.g., first switch 1522 and second switch 1512) modulate locally the tissue impedance by shortcutting the opposite electrodes together. The modulation of each marker (i.e., first marker 1520 and second marker 1120) may be synchronously driven by unique sequence (i.e., code R1 1532 and code R2 1530). The code R1 1532 and the code R2 1530 may be orthogonal to each other. In some embodiments, if additional markers are used that are not on the needle (e.g., implanted markers), the code R1 1532 and the code R2 1530 may be orthogonal to sequences used in other reflectors within the detection volume.

A clock circuit 1538 coupled a sequence generator (not shown) may be used to generate the sequences (e.g., code R1 1532 and code R2 1530). The sequences may provide input signals to open and close the switches 1512 and 1522 to modulate signals reflected by the markers 1510 and 1520 back to a probe based on the code sequence. The sequence generator may be wired to the switches such that the code R1 1532 and the code R2 1530 are provided via wires. For example, code R1 1532 may be delivered to the first switch 1522 via a first set of wires 1534a, 1534b, and the code R2 1530 may be delivered to the second switch 1524 via a second set of wires 1536a, 1536b.

FIG. 16A illustrates a cross-sectional view of the needle 1500 taken through the third electrode 1514 of the second marker 1510. As shown, the needle 1500 may comprise a reinforcement tube 1602 surrounded by an insulation layer 1604. The reinforcement tube 1602 may comprise a conductive material such as stainless steel. The reinforcement tube 1602 may run the entire length of the needle shaft. The insulation layer 1604 may be a non-conductive material that electrically separates the reinforcement tube 1602 from the electrodes. In some embodiments, the insulation layer 1604 may run the entire length of the needle shaft, in other embodiments, the insulation layer 1604 may be positioned along portions of the needle shaft where the markers are located.

As shown in FIG. 16A, the reinforcement tube 1602 may form a lumen 1606. The insulation layer 1604 may surround the reinforcement tube 1602, and an electrode (e.g., the third electrode 1514) may surround the insulation layer 1604. The first set of wires 1534a, 1534b and the second set of wires 1536a, 1536b may be integrated within the insulation layer such that the wires do not contact the reinforcement tube 1602 or the electrodes.

FIG. 16B illustrates a cross-sectional view of the needle 1500 taken through the second switch 1512 of the second marker 1510. The second set of wires 1536a, 1536b are not shown in FIG. 16B because they are connected to the switch as will be discussed with reference to FIG. 16C. In the illustrated embodiment, the second switch 1512 and the pair of leads 1518a and 1518b are located on the exterior of the insulation layer 1604 between electrodes. In some embodiments, the pair of leads 1518a and 1518b and/or the switch may be integrated within the insulation layer 1604. The first set of wires 1534a, 1534b continues to run through the insulation layer 1604 to couple with the first switch 1522 while not interfering with the second switch 1512 or the electrodes of the second marker.

FIG. 16C illustrates a block diagram of the second marker 1510. Note that the first marker 1520 may use the same configuration. For simplicity, the reinforcement tube 1602 surrounded and the insulation layer 1604 are not shown in FIG. 17C. As shown, the switch 1512 may comprise a FET. The set of wires 1536a, 1536b providing the coded sequence input may be coupled to the gate and the source of the switch 1512. The switch 1512 may be coupled to the third electrode 1514 and fourth electrode 1516 via a pair of leads 1518a and 1518b. The input signal may cause the switch 1512 to open and close thereby connecting the third electrode 1514 and fourth electrode 1516 and changing the reflective properties of the marker 1510.
input FIGS. 17-18C illustrate a needle 1700 with markers comprising a pair of plate electrodes. The illustrated embodiment of the needle 1700 uses actively modulated markers and may be used by the systems discussed in relation to FIGS. 1-4 and FIGS. 13-14. However, it is also contemplated that the actively modulated markers may be replaced with passively modulated markers such as discussed with reference to FIGS. 5-8.

As shown in FIG. 17, the needle 1700 may comprise a shaft 1702 with a first marker 1720 and a second marker 1710. The first marker 1720 may be positioned at a first location closer to a proximal end of the needle 1700 and the second marker 1710 may be positioned at a second location closer to a tip of the needle 1700.

The first marker 1720 and the second marker 1710 may reflect signals transmitted by a probe. The first marker 1720 is formed by a pair of electrodes (i.e., first electrode 1724 and second electrode 1726) coupled with a first switch 1722 via a pair of leads 1728a and 1728b. The second marker 1710 is also formed by a pair of electrodes (i.e., third electrode 1714 and fourth electrode 1716) coupled with a second switch 1712 via a pair of leads 1718a and 1718b. The first marker 1720 and the second marker 1710 may be located on opposite sides of the shaft 1702.

The electrodes (i.e., first electrode 1724, second electrode 1726, third electrode 1714, and fourth electrode 1716) may comprise conductive material. The electrodes may be curved to follow the circumference of the needle 1700. In the illustrated embodiment the electrodes are for each marker are located at same point along the needle shaft 1702. As shown, the electrodes are for each marker are spaced along the circumference of the needle with a switch between each pair of electrodes.

When the needle 1700 is inserted into the patient, each of the electrodes are electrically connected to the tissue. The switches (e.g., first switch 1722 and second switch 1712) modulate locally the tissue impedance by shortcutting the opposite electrodes together. The modulation of each marker (i.e., first marker 1720 and second marker 1120) may be synchronously driven by unique sequence (i.e., code R1 1732 and code R2 1730). The code R1 1732 and the code R2 1730 may be orthogonal to each other. In some embodiments, if additional markers are used that are not on the needle (e.g., implanted markers), the code R1 1732 and the code R2 1730 may be orthogonal to sequences used in other reflectors within the detection volume.

A clock circuit 1738 coupled a sequence generator (not shown) may be used to generate the sequences (e.g., code R1 1732 and code R2 1730). The sequences may provide input signals to open and close the switches 1712 and 1722 to modulate signals reflected by the markers 1710 and 1720 back to a probe based on the code sequence. The sequence generator may be wired to the switches such that the code R1 1732 and the code R2 1730 are provided via wires. For example, code R1 1732 may be delivered to the first switch 1722 via a first set of wires 1734a, 1734b, and the code R2 1730 may be delivered to the second switch 1724 via a second set of wires 1736a, 1736b.

FIG. 18A illustrates a cross-sectional view of the needle 1700 taken through the second marker 1710. FIG. 18B illustrates a cross-sectional view of the needle 1700 taken through the first marker 1712. As shown, the needle 1700 may comprise a reinforcement tube 1802 surrounded by an insulation layer 1804. The reinforcement tube 1802 may comprise a conductive material such as stainless steel. The reinforcement tube 1802 may run the entire length of the needle shaft. The insulation layer 1804 may be a non-conductive material that electrically separates the reinforcement tube 1802 from the electrodes. In some embodiments, the insulation layer 1804 may run the entire length of the needle shaft, in other embodiments, the insulation layer 1804 may be positioned along portions of the needle shaft where the markers are located.

As shown in FIG. 18A, the reinforcement tube 1802 may form a lumen 1806. The insulation layer 1804 may surround the reinforcement tube 1802, and the electrodes may be positioned exterior the insulation layer 1804. The first set of wires 1734a, 1734b and the second set of wires 1736a, 1736b may be integrated within the insulation layer such that the wires do not contact the reinforcement tube 1802 or the electrodes.

The second set of wires 1736a, 1736b are not shown in FIG. 18B because they are connected to the switch as will be discussed with reference to FIG. 18C. In the illustrated embodiment, the second switch 1712 and the pair of leads 1718a and 1718b are located on the exterior of the insulation layer 1804 between electrodes. In some embodiments, the pair of leads 1718a and 1718b and/or the switch may be integrated within the insulation layer 1804. The first set of wires 1734a, 1734b continues to run through the insulation layer 1804 to couple with the first switch 1722 while not interfering with the second switch 1712 or the electrodes of the second marker.

FIG. 18C illustrates a block diagram of the second marker 1710. Note that the first marker 1720 may use the same configuration. For simplicity, the reinforcement tube 1802 surrounded and the insulation layer 1804 are not shown in FIG. 17C. As shown, the switch 1712 may comprise a FET. The set of wires 1736*a*, 1736*b* providing the coded sequence input may be coupled to the gate and the source of the switch 1712. The switch 1712 may be coupled to the third electrode 1714 and fourth electrode 1718 via a pair of leads 1718*a* and 1718*b*. The input signal may cause the switch 1712 to open and close thereby connecting the third electrode 1714 and fourth electrode 1718 and changing the reflective properties of the marker 1710.

FIG. 19 illustrates an embodiment in which the needle 1900 is used to transmit a signal. The needle 1900 may comprise a port 1902 to receive a transmit signal. In the illustrated embodiment, the port 1902 is a coaxial port configured to receive a coaxial feed. The transmit signal may be a series of pulses.

The port 1902 may receive the transmit signal and feed the needle shaft. The needle shaft may comprise a conductive material such as stainless steel. In some embodiments, the center conductor of the coaxial feed directly couples with the needle shaft. A proximal portion of the needle shaft may comprise the conductive material surrounded by an insulation sheath 1906. The insulation sheath 1906 may be a thin non-conductive material to insulate the metal shaft from coming into contact with the surrounding tissue.

A distal portion of the needle shaft may comprise an exposed tip 1904. The exposed tip 1904 may comprise the conductive material without the insulation sheath 1906. The exposed tip 1904 may act as a transducer coupling the transmit pulse to the tissue. The length of the exposed tip 1904 may be optimized to better transmit pulses to the tissue.

The following is an example of how the needle 1900 may be used. The needle 1900 may be inserted into tissue. A transmit pulse is sent from a pulse generator to the needle 1900 and the exposed tip 1904 transmits the pulse. A multi-antenna probe such as described in the previous figures can receive the transmit pulse and from the delay times to each of the receive antennas, the exact distance and three-dimensional location of the exposed tip 1904 can be calculated as described previously. The transmit pulse can also be sent to a center antenna to obtain a reference cross-talk pulse to determine the face of the multi-antenna disk. In some embodiments, background noise can be subtracted by taking a sample with no transmit pulse and subtracting it from a sample with a transmit pulse.

Additionally, in some embodiments, the localization system may have the ability to track a location of the probe and adjust the orientation of the coordinates based on the probe location. For example, in some embodiments, the probe may include a gyroscope and an accelerometer to track the location and orientation of the probe. As the localization system changes position, the interface displayed may rotate to provide a corresponding view change. Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to an "embodiment" means that a particular feature, structure, or characteristic described in connection with that embodiment is included in at least one embodiment. Thus, references to embodiments throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A system for localization of a needle, the system comprising:

a needle comprising:

a handle;

a shaft coupled to the handle;

a first marker comprising a first pair of electrodes and a first switch, wherein the first switch is coupled to a first side of the shaft; and a second marker comprising a second pair of electrodes and a second switch, wherein the second switch is coupled to a second side of the shaft that is opposite the first side of the shaft;

an insulation layer covering at least a portion of the shaft;

wires connected to each of the first marker and the second marker extending along the shaft from the first marker and the second marker to the handle within the insulation layer, wherein the wires connected to the first marker extend along the first side of the shaft and the wires connected to the second marker extend along the second side of the shaft;

a probe comprising:

a transmit antenna for transmitting electromagnetic signals into a patient's body;

a receive antenna for receiving reflected signals from the first marker and the second marker within a patient's body;

a modulation controller external to the needle and the first marker and the second marker, the modulation controller coupled to the needle via a cable that interfaces with the wires for each of the first marker and the second marker for electrical communication with the first marker and the second marker, wherein the modulation controller causes the switch of the first marker and the second marker of the needle to open and close to modulate the electromagnetic signals reflected by the first marker and the second marker; and one or more processors configured to:

process the reflected signals from the first marker and the second marker;

determine a location of the first marker and the second marker based on the reflected signals; and determine a position of a tip of the needle based on the location of the first marker and the second marker.

2. The system of claim 1, wherein each of the first marker and the second marker comprise a pair of cylindrical electrodes on the exterior of the insulation layer.

3. The system of claim 1, wherein each of the first marker and the second marker comprise two cylindrical electrodes on the exterior of the insulation layer, wherein the two cylindrical electrodes are spaced along a length of the needle and the two cylindrical electrodes are coupled via a circuit comprising a switch that opens and closes to modulate electromagnetic signals reflected by the first marker and the second marker.

4. The system of claim 1, wherein each of the first marker and the second marker comprise two curved electrodes on the exterior of the insulation layer, wherein the two curved electrodes are spaced along a circumference of the needle and the two curved electrodes are coupled via a circuit comprising a switch that opens and closes to modulate electromagnetic signals reflected by the first marker and the second marker.

5. The system of claim 1, wherein to determine the position of the tip of the needle, the one or more processors are further to calculate coordinates of the tip based on a distance between the first marker and the second marker and the tip.

6. The system of claim 1, wherein the first marker and the second marker modulate the reflected signals such that modulation of each marker is synchronously driven by a unique sequence, wherein the unique sequence is orthogonal to other sequences used in the other marker.

7. A system for localization of a needle, the system comprising:

a needle comprising a shaft comprising a first conductive cylindrical section, a second conductive cylindrical section, and a non-conductive cylindrical portion, wherein the first conductive cylindrical section, the second conductive cylindrical section, and the non-conductive cylindrical portion are coupled together to form a lumen of the shaft of the needle that extends through the first conductive cylindrical section, the second conductive cylindrical section, and the non-conductive cylindrical portion, wherein a first end of the non-conductive cylindrical portion is coupled to the first conductive cylindrical section, and a second end of the non-conductive cylindrical portion is coupled to the second conductive cylindrical section such that the non-conductive cylindrical portion is between the first conductive cylindrical section and the second conductive cylindrical section;

one or more markers, coupled the shaft, wherein the one or more markers comprise a switch that selectively electrically couples the first conductive cylindrical section to the second conductive cylindrical section;

a probe comprising:

a transmit antenna for transmitting electromagnetic signals into a patient's body;

a receive antenna for receiving reflected signals from the one or more markers within a patient's body; and one or more processors configured to:

process the reflected signals from the one or more markers;

determine a location of the one or more markers based on the reflected signals; and determine a position of a tip of the needle based on the location of the one or more markers.

8. The system of claim 7, further comprising:

a first lead electrically coupling the first conductive cylindrical section of the shaft to the switch; and a second lead electrically coupling the second conductive cylindrical section of the shaft;

wherein opening and closing the switch modulates electromagnetic signals reflected by the first conductive cylindrical section and the second conductive cylindrical section of the shaft.

* * * * *